(12) United States Patent
Sethumadhavan et al.

(10) Patent No.: US 10,964,434 B2
(45) Date of Patent: Mar. 30, 2021

(54) SYSTEMS AND METHODS FOR EXTRACTION OF CLINICAL KNOWLEDGE WITH REIMBURSEMENT POTENTIAL

(71) Applicant: Apixio, Inc., San Mateo, CA (US)

(72) Inventors: Vishnuvyas Sethumadhavan, Mountain View, CA (US); Mary Ellen Campana, San Mateo, CA (US); Robert Derward Rogers, Pleasanton, CA (US); Shahram Shawn Dastmalchi, San Ramon, CA (US)

(73) Assignee: APIXIO, INC., San Mateo, CA (US)

( * ) Notice: Subject to any disclaimer, the term of this patent is extended or adjusted under 35 U.S.C. 154(b) by 913 days.

(21) Appl. No.: 14/872,082

(22) Filed: Sep. 30, 2015

(65) Prior Publication Data
US 2016/0098526 A1  Apr. 7, 2016

Related U.S. Application Data

(63) Continuation of application No. 13/769,254, filed on Feb. 15, 2013, now abandoned, which is a continuation-in-part of application No. 13/223,228, filed on Aug. 31, 2011, now Pat. No. 10,176,541, and
(Continued)

(51) Int. Cl.
*G16H 10/60* (2018.01)
*G16H 50/30* (2018.01)
*G16H 50/70* (2018.01)
*G06F 19/00* (2018.01)
(Continued)

(52) U.S. Cl.
CPC ............. *G16H 50/30* (2018.01); *G06F 19/00* (2013.01); *G06Q 10/10* (2013.01); *G16H 10/60* (2018.01); *G16H 15/00* (2018.01); *G16H 50/70* (2018.01)

(58) Field of Classification Search
CPC ...................................... G06Q 50/22
See application file for complete search history.

(56) References Cited

U.S. PATENT DOCUMENTS 6,209,095 B1 * 3/2001 Anderson .......... G06Q 20/3674
713/176
6,266,645 B1 * 7/2001 Simpson ................ G16H 40/20
705/3
6,505,196 B2 1/2003 Drucker et al.
(Continued)

FOREIGN PATENT DOCUMENTS

JP 4471736 B2 3/2010
JP 2010-134946 A 6/2010
KR 10-0750071 B1 8/2007

OTHER PUBLICATIONS

Korean Intellectual Property Office, ISA, "International Search Report and Written Opinion" in PCT Application No. PCT/US2013/022813, dated May 30, 2013, 10 pages.

*Primary Examiner* — Robert A Sorey
*Assistant Examiner* — Kristine K Rapillo
(74) *Attorney, Agent, or Firm* — Kang S. Lim

(57) ABSTRACT

A computerized Medical Information Navigation Engine ("MINE") extracts clinical knowledge, by identifying coded elements with reimbursement potential contributing to payoff based on clinical history, and subtracting coded elements documented in an encounter from the coded elements, based on business logic. The MINE sorts the remaining coded elements in accordance with one optimization criteria to payoff based on clinical history.

23 Claims, 33 Drawing Sheets

Related U.S. Application Data a continuation-in-part of application No. 13/747,336, filed on Jan. 22, 2013, now abandoned.

(60) Provisional application No. 61/600,994, filed on Feb. 20, 2012, provisional application No. 61/590,330, filed on Jan. 24, 2012, provisional application No. 61/379,228, filed on Sep. 1, 2010.

(51) Int. Cl.
*G16H 15/00* (2018.01)
*G06Q 10/10* (2012.01)

(56) References Cited

U.S. PATENT DOCUMENTS

| | | | |
|---|---|---|---|
| 6,874,085 B1* | 3/2005 | Koo | H04L 63/0428 713/165 |
| 2003/0004748 A1* | 1/2003 | Coleman | G06Q 10/06398 705/7.34 |
| 2005/0137912 A1* | 6/2005 | Rao | G06Q 10/10 705/4 |
| 2006/0036619 A1 | 2/2006 | Fuerst et al. | |
| 2006/0047669 A1 | 3/2006 | Durrence et al. | |
| 2006/0241978 A1 | 10/2006 | Yoshii | |
| 2006/0265251 A1* | 11/2006 | Patterson | G06Q 40/08 705/3 |
| 2007/0083390 A1 | 4/2007 | Gorup et al. | |
| 2008/0091633 A1* | 4/2008 | Rappaport | G06N 5/022 706/50 |
| 2008/0270340 A1 | 10/2008 | Abrams et al. | |
| 2009/0024615 A1 | 1/2009 | Pedro et al. | |
| 2009/0048877 A1 | 2/2009 | Binns et al. | |
| 2009/0070103 A1 | 3/2009 | Beggelman et al. | |
| 2009/0112882 A1 | 4/2009 | Maresh et al. | |
| 2009/0136102 A1 | 5/2009 | Kimpe et al. | |
| 2009/0271221 A1 | 10/2009 | Aridi et al. | |
| 2010/0131482 A1 | 5/2010 | Linthicum et al. | |
| 2010/0185496 A1 | 7/2010 | Hahn et al. | |
| 2011/0072002 A1* | 3/2011 | Kirkby | G06F 16/958 707/711 |
| 2011/0196702 A1 | 8/2011 | Hani et al. | |

\* cited by examiner

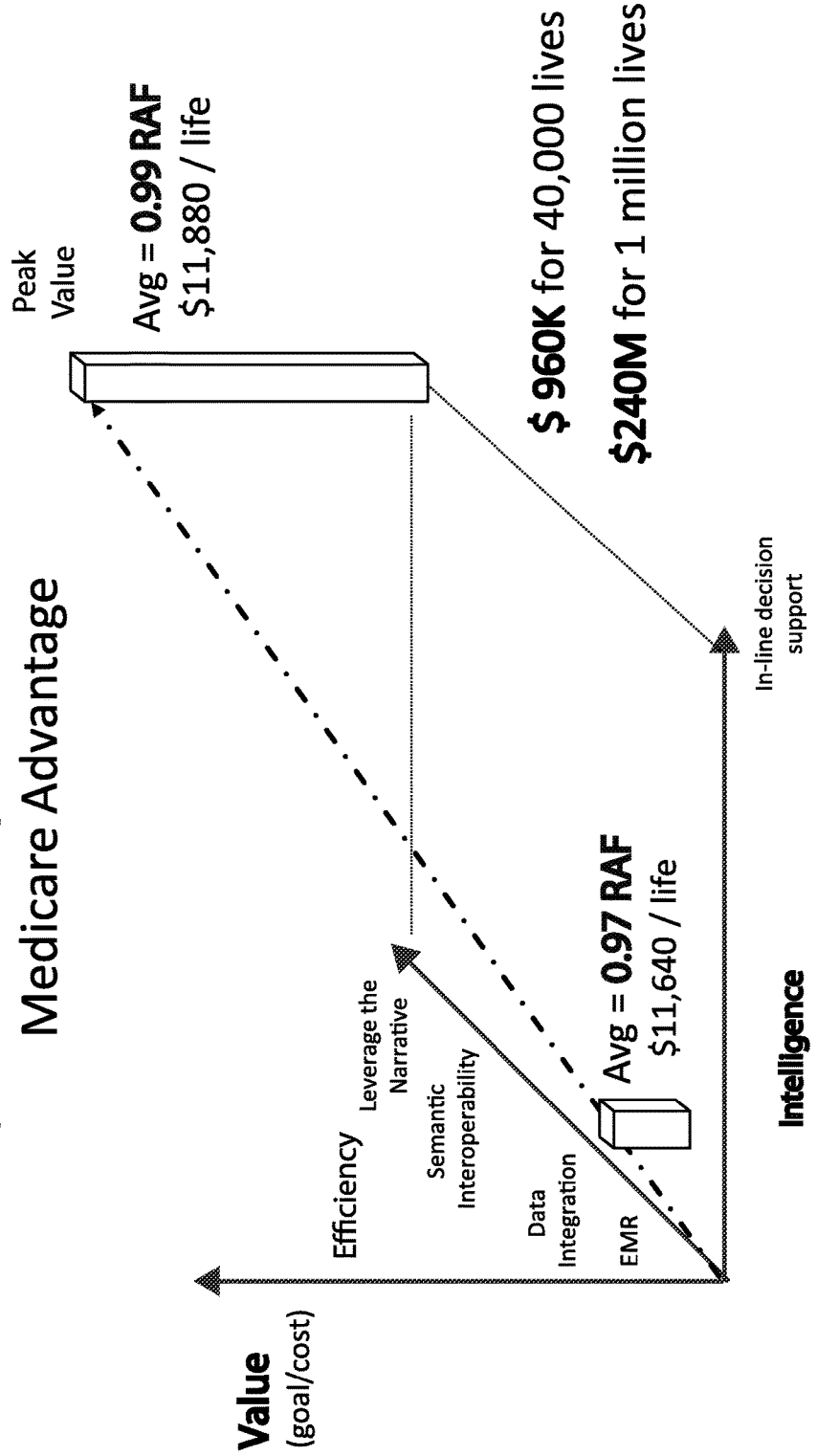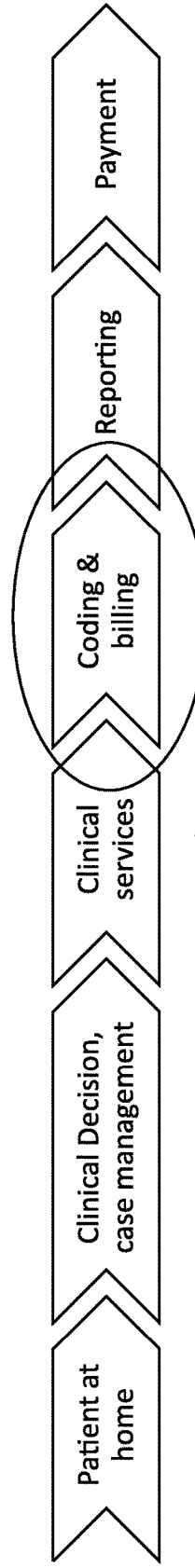
Fig. 10

APIXIO™

| | | Upload Feedback Log Out |
|---|---|---|
| Patient Information | | Chris Cardio MDS ▼ |
| Problems 1 | | |
| Labs 51 | [Test Patient ✗] CHF\| | Search 🔍 |

Show entire record

Find additional matches

Related results
- ⊕ inflammation bug
- ⊕⊕ cardiac echo
- ⚠ caII - chronic airfl...
- ⊕⊕ arteriosclarosis cor...
- ⊕ af
- ⊕⊕ rhonchi
- ⊕⊕ chest exclusion x-ray
- ⊕⊕ accident - cerebrova...
- ⊕⊕ anaemia
- ⊕⊕ chest creptition
- ⊕ angst Patient Information

| Name: | Test Patient | Phone: | (650)555-0000 (H) |
|---|---|---|---|
| DOB: | 01/02/1930 | Address: | 1825 S. Grant Street |
| Sex: | F | | San Mateo CA 94402 |

Update Care Team
Invite to myApixio

Problems

DM ①

Labs

| AST | 28 | 10 - 35 U/L | 05/18/2010 | ⑤ |
| Albumin | 4.1 | 3.6 - 5.1 g/dL | 05/18/2010 | ⑤ |
| Alkaline Phosphatase | H 155 | 33 - 130 U/L | 05/18/2010 | ⑤ |
| Chloride | 104 | 98 - 110 mmol/L | 05/18/2010 | ⑥ |
| Creatinine | 1.01 | 0.63 - 1.22 mg/dL | 05/18/2010 | ⑥ |
| Potassium | 4.1 | 3.5 - 5.3 mmol/L | 05/18/2010 | ⑥ |
| Sodium | 140 | 135 - 146 mmol/L | 05/18/2010 | ⑥ |
| Urea Nitrogen | 25 | 7 25 mg/dL | 05/18/2010 | ⑥ |
| eGFR | L 52 | >=60 - >=6 mL/min | 05/18/2010 | ⑥ |
| Cholesterol | 181 | 125 - 200 mg/dL | 05/07/2010 | ③ |
| Cholesterol/HDL | 1.7 | or=5 - or=5 ratio | 05/07/2010 | ③ |
| HDL Cholesterol | 105 | >or=46 - >or=46 mg/dL | 05/07/2010 | ② |
| Hematocrit | L 31.9 | 35 - 45 % | 05/07/2010 | ② |
| Hemoglobin | L 11.1 | 11.7 - 15.5 g/dL | 05/07/2010 | ⑤ |
| LDL Cholesterol | 59 | 130 - 130 mg/dL | 05/07/2010 | ② |
| MCH | 29.2 | 27 - 33 pg | 05/07/2010 | |
| MCHC | L 31.9 | 32 - 36 g/dL | 05/07/2010 | ② |

APIXIO™

| | | | Upload Feedback Log Out |
|---|---|---|---|
| | Joseph Sample✗ bw| | Search 🔍 | Ingrid Internist MD ▶ |

Patient Information

Health Status  1

Show entire record

---

Patient Information

| | | | | Find additional matches |
|---|---|---|---|---|
| Name: | Joseph Sample | Phone: | 415-555-5555 (H) | ② |
| DOB: | 10/12/1943 | Address: | 1 Mission Blvd | |
| Sex: | U | | San Francisco, CA 94111 | |

Update Care Team
Invite to myApixio

Health Status

Joseph Sample: My body weight is 126lbs today. 12/09/2011. *(02/16/2012 10:47am gmt-08:00)*

Respond to patient

Joseph Sample: BW: 128 lbs. 12/12/2011 . *(02/16/2012 12:18pm gmt-08:00)*
Joseph Sample: BW: 128 lbs. today12/11/2011 . *(02/16/2012 12:17pm gmt-08:00)*
Joseph Sample: BW: 128 lbs. today12/10/2011 . *(02/16/2012 12:16pm gmt-08:00)*
Nurse Nelly : For your CHF, please record BW daily. Thank you. *(02/16/2012 10:46am gmt-08:00)*

Copyright © 2012 Apixio, Inc. All rights reserved | 2.0 Beta1-SNAPSHOT-0

FIG. 31 condition.

6. DM - Diet controlled diabetes. Excellent. HgAIC 5.0 with fasting glucose <100. Saw Dr T for endocrine. Diet control. Sees optho regularly (also has history of dry macular degeneration) Due for optho visit and will schedule.

7. Hyperlipidemia. Controlled on medication. LDL and HDL excellent

8. Hyperparathyroidism and Vit D deficiencymuch improved on recent labs. Normal Vit D and PTH decreased. She wishes to see a new endocrinologist- refer to Dr S HCC cde: 19 - Diabetes without Complication and ICD9: | Please select an ICD9 ▼

Please select an ICD9
249.00 - Secondary diabetes mellitus without mention of complication, not stated as uncontrolled
249.01 - Secondary diabetes mellitus without mention of complication, uncontrolled
250.00 - Diabetes mellitus without mention of complication, type II or unspecified type, nc
250.01 - Diabetes mellitus without mention of complication, type I or liuvenile type1, not stated a

FIG. 32

SYSTEMS AND METHODS FOR EXTRACTION OF CLINICAL KNOWLEDGE WITH REIMBURSEMENT POTENTIAL

CROSS REFERENCE TO RELATED APPLICATIONS

This application is a continuation of and claims priority to U.S. patent application Ser. No. 13/769,254, of the same title, filed Feb. 15, 2013, currently pending, which is a continuation-in-part application claims the benefit of U.S. Provisional Application No. 61/600,994 filed on Feb. 20, 2012, entitled "Clinical Knowledge Extraction, Provider-Guided Educational Material and Top of Mind Concepts for Patient".

Also, application Ser. No. 13/769,254 is a continuation-in-part application claims the benefit of application Ser. No. 13/223,228 filed on Aug. 31, 2011, entitled "Medical Information Navigation Engine (MINE) System", which application claims priority to U.S. Provisional Application No. 61/379,228 filed on Sep. 1, 2010, of the same title.

Additionally, application Ser. No. 13/769,254 is a continuation-in-part application claims the benefit of application Ser. No. 13/747,336 filed on Jan. 22, 2013, entitled "Knowledge Extraction and Exchange Method and Apparatus", which application claims priority to U.S. Provisional Application No. 61/590,330 filed on Jan. 24, 2012, of the same title.

All above-listed applications are fully incorporated in their entirety by this reference.

BACKGROUND

The present invention relates generally to a medical information engine, and particularly to management and consolidation of medical information which enables computation of payoffs that track encounters.

Despite rapid growth of innovation in other fields in recent decades, the world of medical information, including patient medical records, billing, referrals, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One of the challenges facing those in the medical or related areas is the number of sources of information, the great amount of information from each source, and consolidation of such information in a manner that renders it meaningful and useful to those in the field in addition to patients. Obviously, this has contributed to increased medical costs and is perhaps largely attributed to the field suffering from an organized solution to better aid the medical professionals, to better aid those requiring more reliable patient history and those requiring more control and access over such information.

Currently, payoffs for medical encounters are not tied to the outcome. A physical therapy session is paid the same regardless of if the patient gains added function or not. This incentivizes providers to be inefficient, and prioritize quantity of care over the quality of care.

It is therefore apparent that an urgent need exists for a medical information navigation engine ("MINE") capable of managing medical information in a manner that is enables the calculation of payoffs in response to the outcome of an encounter. Such a system will increase care efficiency and increase care quality.

SUMMARY

To achieve the foregoing and in accordance with the present invention, systems and methods for managing medical information are provided. In particular, systems and methods for a Medical Information Navigation Engine ("MINE") is provided which can compare actual patient encounters with optimal encounters to generate a payoff.

In one embodiment, a computerized Medical Information Navigation Engine ("MINE") is configured to extract clinical knowledge, by identifying a plurality of coded elements with reimbursement potential contributing to payoff based on clinical history, and subtracting coded element(s) documented in an encounter from the plurality of coded elements, wherein the subtracting is based on business logic. The MINE can also be configured to sort a remainder of the plurality coded elements in accordance with one optimization criteria to payoff based on clinical history. The MINE processes the sorted remainder of the plurality of coded elements in a knowledge exchange, and provides the processed sorted remainder of the plurality of coded elements to a user.

In some embodiments, the reimbursement potential includes at least one of contribution to payoff and previously rejected claims, the rejected claims rejected based on claim duplication, claim invalidity and/or improper claim format. The business logic can include encounter documentation, code hierarchy supersession and/or healthcare provider validation. Optimization criteria can include potential for payoff, contribution to patient risk and/or likelihood of accuracy. The potential for payoff can be derived from potential reimbursement value. The contribution to patient risk can include at least one patient risk adjustment factor (RAF).

The MINE can also be further configured to format the processed sorted remainder of the plurality of coded elements into a format acceptable by at least one of a payer and/or an auditor. The processed sorted remainder of the plurality of coded elements may be validated by the user. The MINE can also be configured to tracking user presentation and/or user selection. The sorted remaining sorted coded elements can be stored in a knowledge exchange for future rankings.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIGS. 9-11 each show a graph of the intelligence, shown in the x-direction, versus value, shown in the y-direction, of various performance improvements realized using the various methods and embodiments of the invention;

Figure 29:
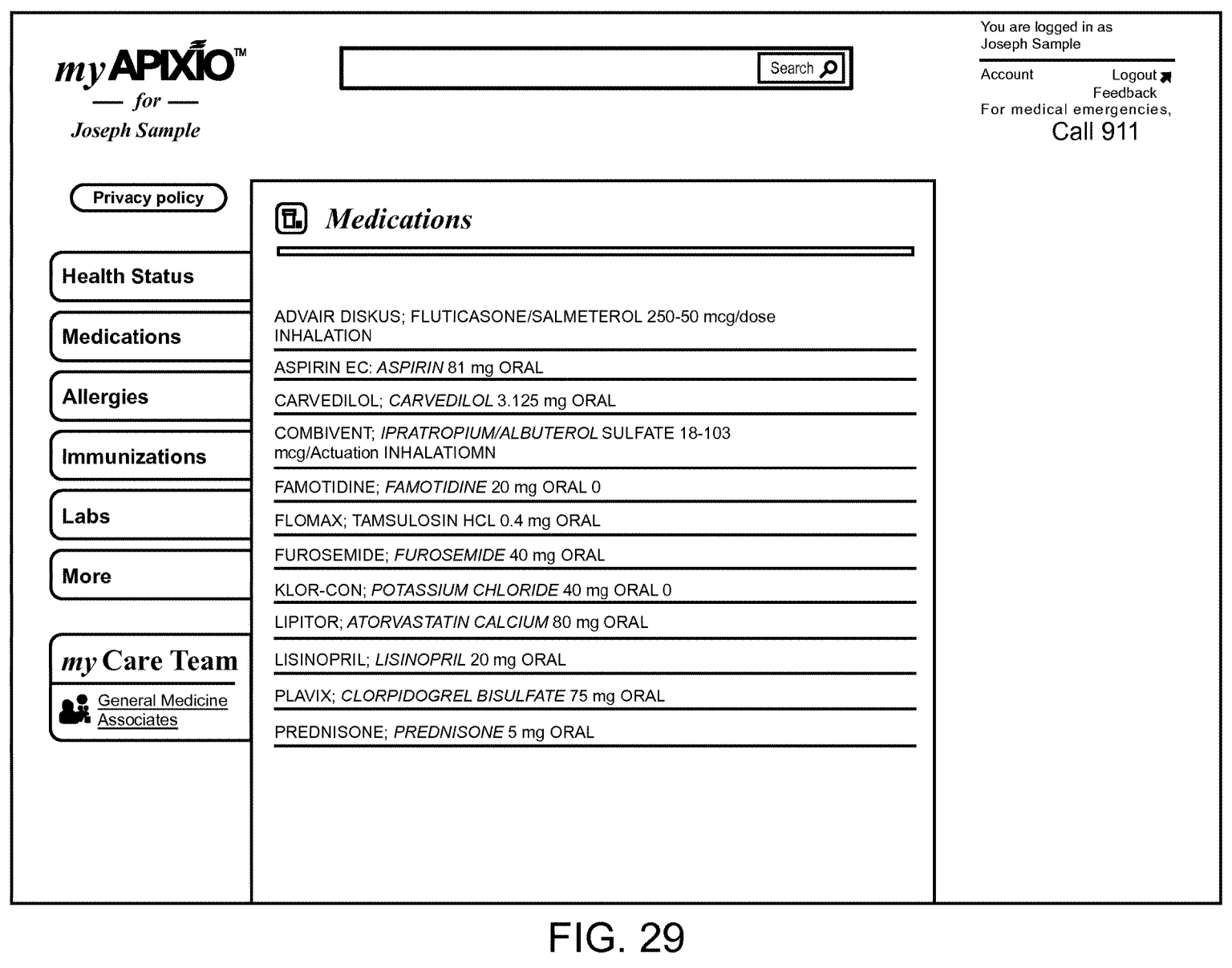

FIGS. 26-31 are exemplary screen shots (screens) illustrating the results obtained when executing the flowcharts 23-25; and FIG. 32 is a screenshot illustrating text mining for solving the HCC coding problem.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "only," "first," "initially," "next," "subsequently," "before," "after," "lastly," and "finally," are not meant to limit the scope of the present invention as the embodiments disclosed herein are merely exemplary.

Figure 1:
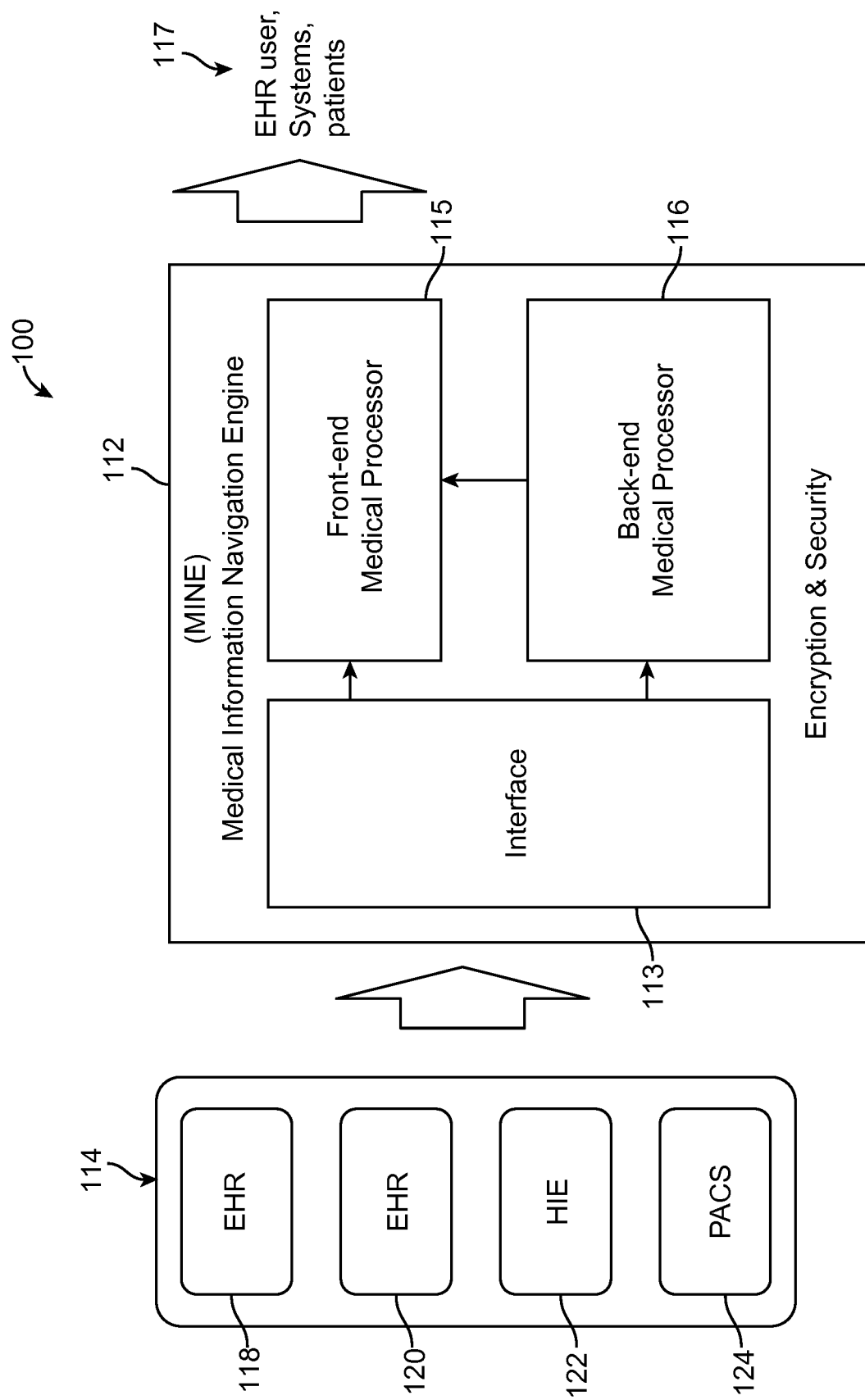
FIG. 1 shows a medical system 100, in accordance with an embodiment of the invention.

Referring now to FIG. 1, medical system 100, in accordance with an embodiment of the invention. The system 100 is shown to include medical source 114, a medical information navigation engine (MINE) 112, and medical information consumers (also referred to herein as "output" or "medical output") 117. The medical source 114 are shown to include an electronic health record (EHR) 118, EHR 120, health information exchange (HIE) 122, and a picture archiving and communication system (PACS) 124. The MINE 112 is shown to include interface 113, a back-end medical processor 116, and a front-end medical processor 115.

"Medical information", as used herein, refers to any health-related information, including but not limited to patient medical records, patient entered information, care team entered information, healthcare device generated information, and billing information.

The source 114 generally provides various medical information to the MINE 112. For example, the EHRs 118 and 120 each may provide information such as medical records and billing, the HIE 122 may provide information such as medical records, and the PACS 124 may provide information such as diagnostic imaging and reports.

The medical information consumers 117, which may be made of a host of entities or individuals, such as patients, clinics, medical institutions, health organization, and any other medical-related party, use information that is provided by the processor 115 of MINE 112 and that can, by way of example, consist of patients, medical systems, medical organization administrators, medical researchers, and/or EHR users. For example, user-customized processed medical information is provided by the processor 115 to a number of users within the medical information consumers 117. In this case, the processor 115 generates user-customized processed medical information to a plurality of users, with at least a portion of the user-customized processed medical information being provided to each of the users based on the relevancy of the portion being provided of each user's specific function or role and each user's associated security privileges.

The processor 116, in some embodiments, indexes identifies, maps, and consolidates medical information, received from the interface 113, and tags this information, and determines to reconcile the tagged information. In some methods and embodiments, information that is extracted from images is tagged to enhance recall of search queries. Indexing, at least in part, processes documents and converts them into formats that allows for quick searching across a large collection of documents.

The information in the MINE 112 is encrypted and secure to ensure privacy of sensitive medical information.

It is understood that the sources 114 of FIG. 1 includes merely some examples of the sources that communicate with the MINE 112 and that other sources, known to those in the field, are contemplated. Similarly, the output 117 may be used by those or entities not discussed herein but that are contemplated and within the scope and spirit of the invention.

The interface 113 serves to receive information that is in various forms, such as but not limited to text, html, CCD, CCR, HL7 and any other type or formatted information. The interface 113 then provides to the processors 115 and 116 information, as needed.

The processor 116 receives some of the medical information that the interface 113 processes and performs certain tasks to process it, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others.

One aspect of consolidation, reconciliation and de-duplication, generally refers to removing of redundant patient medical records, such as, multiple records for the same individual appearing as though the records are for different individuals or multiple data elements that are recorded similarly but slightly differently in the different sources. In this case, the processor 116 recognizes that the records belong to a single individual or are the same data and just recorded differently and automatically consolidates them. The patient or a user of the system 100 may also manually perform reconciliation. The processor 116 advantageously determines whether or not reconciliation is performed.

The processor 116 outputs the indexed, tagged and reconciled information to the processor 115. The foregoing tasks are a generalization and further details of each are provided below.

The processor 115 performs certain tasks on the information provided by the interface 113 and the processor 116, which include query, search, presentation, and quality checking. The output of the processor 115 is the output of the MINE 112, or output 117.

The MINE 112, through the processor 115, in some embodiments and methods, invites members of a medical care team to join it thereby allowing distributed user-organized care teams.

Querying, as performed by the processor 115, is the ability to receive, as input, a free text query, from a user, (i.e., a query without any restrictions on the structure)—and converting the free text query into commands to a medical search engine, such as Medical Lexical Search Engine and the MATRIX (Medical Application Terminology Relationship IndeX) Concept Search Engine, using a sophisticated query processing engine optimized to work with medical queries. The results of the search engine are sent to the presentation display planner—which decides the most relevant presentation given the user's organization and role (e.g. the provider, search query program, a healthcare administrator, a study administrator, and the patient). The presentation discussed below, receives such information. In some embodiments and methods, the medical information or user information is processed to suggest relevant queries.

Search, as performed by the processor 115, is built around the concept of Zero-Click Relevance—or the ability to get to all the relevant information an actor in the healthcare system requires by typing in just a single query. The search engine, within the processor 115, performing the search comprises an indexing and searching, as will become apparent shortly. Optionally, search results may be securely embedded into third party programs. In some embodiments, searching involves determining presenting (also referred to herein as "providing") access to specific relevant data based on a search query, the patient, and the user's specific function and/or role and security privileges. A user may be within the output 117 and security privileges are either determined by the MINE 112 or by the patient or both. The information that is uploaded to the MINE 112 by users, such as in output 114 (in some embodiments) is searched by the processor 115. The uploaded information may include information such as but not limited to status posts, records, and images. Such user-uploaded information is routed automatically to the output 117, as needed.

Some aspects of the search are now discussed relevant to an example. Assuming, by way of example, that Dr. Smith, an internal medicine physician, sees a new patient, Joan Sample, who presents with a complaint of chest pain. Joan has brought several continuity-of-care documents (CCDs) and a 600-page pdf file representing of her medical chart. She has seen a cardiologist who uses NextGen's electronic medical record (EMR) and a gastroenterologist who uses eMD's EMR and she has recently visited a local emergency room. Dr. Smith uses the search of the various methods and embodiments of the invention to efficiently assemble the relevant information he needs. Dr. Smith selects Joan Sample as the patient and enters the clinical context "chest pain" in the search bar of a screen presented by the MINE 112 (examples of such screens are shown in subsequent figures herein). He is presented with relevant lab results, such as CKMB, troponin, and amylase, relevant diagnostic results, such as prior electrocardiograms (EKGs) and the most recent chest computed tomography (CT) scan; and all progress notes and consult reports in which concepts relevant to chest pain, like "GERD" and "cardiac stress test", are mentioned. Two distinct types of searches are combined, in accordance with a method and embodiment of the invention, to retrieve information medically relevant to Joan's complaint: 1) Lexical search, where text in the patient record is searched for occurrences of the search term, its variants and synonyms; and 2) Medical concept search, where data that is medically related to the search term is retrieved. Medical concept search finds relevant structured data with standardized codes, such as lab results, and text results, such as progress notes, which include terms medically related to the search term. In Joan's case, a search for "chest pain" returns a CKMB lab result and a reference to the most recent chest CT scan. Accordingly and advantageously, the Lexical and Medical concept search solves Dr. Smith's information overload problem by returning information in the chart most relevant to determining the etiology of Joan's chest pain complaint. Further, in some embodiments, the presentation, discussed shortly, presents a united view of Joan's history by reconciling and de-duplicating data from multiple sources that may be coded and described differently. Redundant data is automatically reconciled even if it is described differently by differently sources.

Presentation, as performed by the processor 115, is displaying health information to the requesting user in a way that reduces the number of clicks and maximizes the amount of meaningful information delivered based on the interpreting the intent of the user query.

Quality checking 230, as performed by the processor 115, is checking of the quality of medical information provided by various sources, i.e. source 114, by the patients, structured data, and unstructured data, in a Wiki-like mannered setting whereby the users can help maintain and improve the quality of information displayed. The foregoing tasks, performed by the processor 115, are further described in detail below. Additionally, the users or patients may make comments regarding medical information, in a Wiki-like manner.

In summary, the MINE 112 transacts medical information including the interface 113 receiving medical information from a number of medical sources (such as within the source 114) for processing, identifying, mapping, and consolidating by the medical processor 116, providing access to specific relevant data, based on a user's security privileges, within the identified, mapped, and consolidated medical information, based on user-specific functions or roles, performed by the processor 115, and generating user-customized processed medical information to a number of users, such as within the output 117, with at least a portion of the user-customized processed medical information being provided to each of the users based on its relevancy to each user's specific function or role and each user's associated security privileges.

Figure 2:
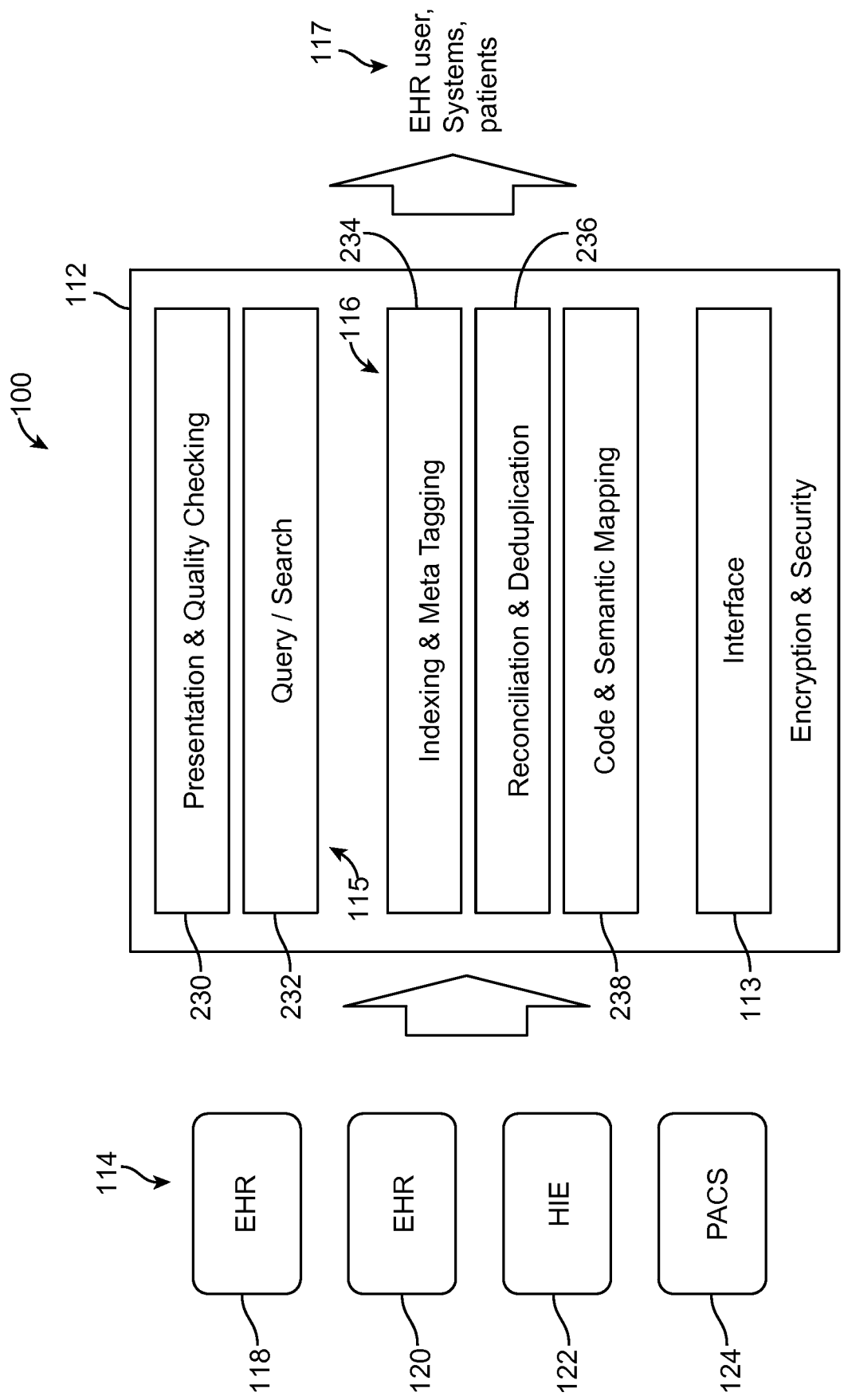
FIG. 2 shows further details of the system 100, particularly the MINE 112 thereof.

FIG. 2 shows further details of the system 100, particularly the MINE 112 thereof. That is, the processor 116 is shown to include an indexing and metal tagging module 234, which includes an indexing module and a meta tagging module (both of which are not shown in FIG. 2 in the interest of clarity), which may be a module, as shown in FIG. 2 or two physically separate modules. The processor 116 is further shown to include a reconciliation and de-duplication module 236, which also can be broken out into two modules, a reconciliation module and a de-duplication module, and a code and semantic mapping module 238, which also may be a single module or multiple modules. The modules 234, 236, and 238 communicate with one another.

The processor 115, in some embodiments, includes display and visualization 340 executing on one or more servers 238, which may be any suitable computing engine, similar to the servers 232, including but not limited to PCs or servers. The display 340 is used to construct presentation and display information to users, such as the patient's records, billing information, and other types of medical information. The display 340, in some embodiments, also performs processing of some of the functions of the processor 115.

The foregoing modules may be software programs, executed by a computer or computing engine of suitable sorts, or may be implemented in hardware.

Figure 3:
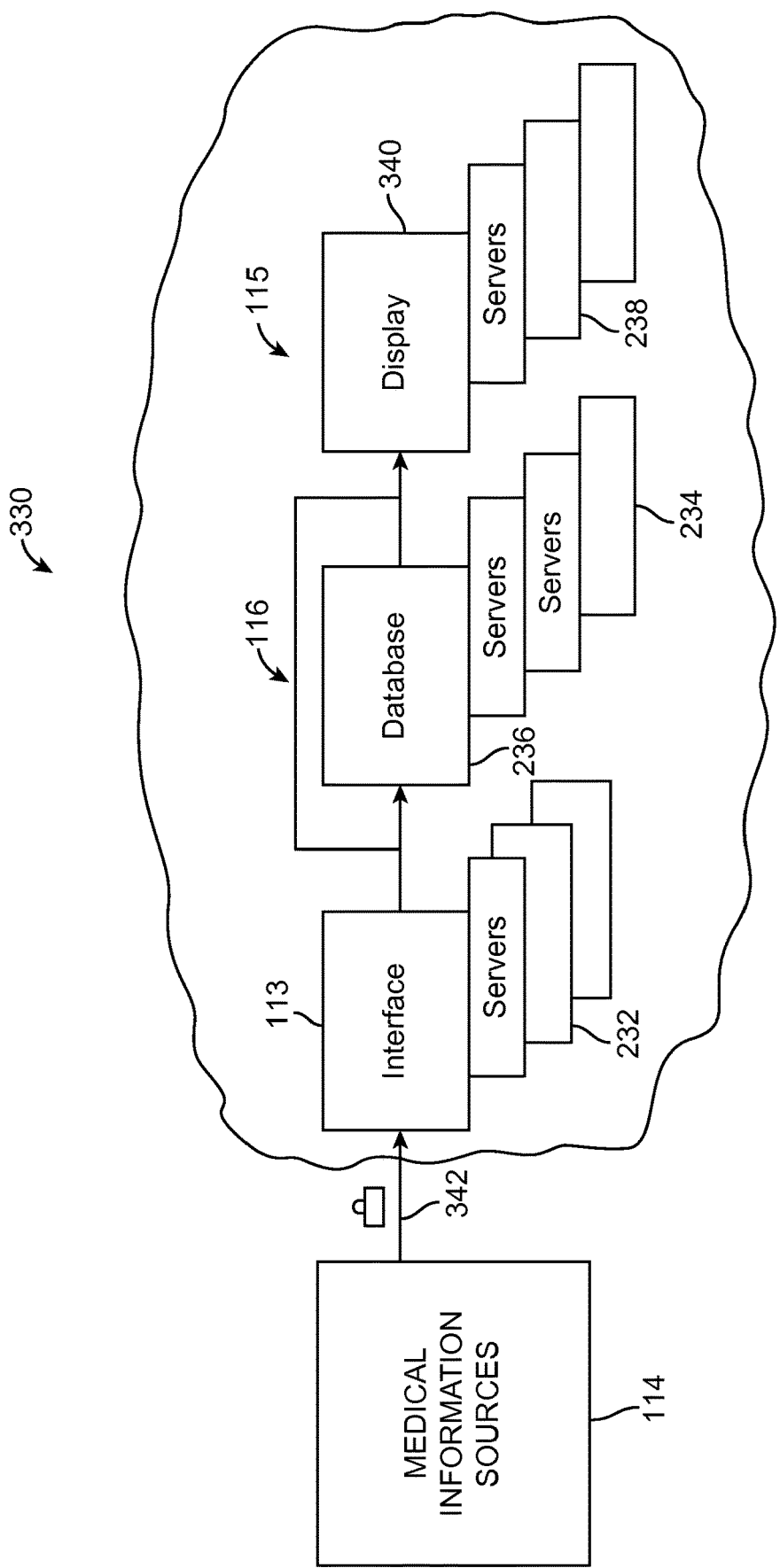
FIG. 3 shows an exemplary embodiment implementing the system 100 using various devices.

FIG. 3 shows an exemplary embodiment implementing the system 100 using various devices. That is, the medical system 330 is analogous to the system 100 and is shown to include the sources 114 coupled to communicate, securely, through the secure communication link 342, to the interface 113. The link 342 may be any suitable communication channel allowing information, of various formats and types, to be transferred to the interface 113 in a secure and encrypted fashion. Exemplary communication channels of which the link 342 is made include the Internet, VPN connections over the Internet, private dedicated digital lines such as T1, T3, E1, E3, SONET, and other fiber optic formats.

The interface 113, in some embodiments, is a software program that executes on one or more servers 232, which can be a server of any kind of suitable computing engine, such as personal computer (PC). The servers 232 receive secure information through the link 342 from the sources 114. The processor 116, in some embodiments, includes the module 236 and one or more servers 234, which may be any suitable computing engine, similar to the servers 232, including but not limited to PCs or servers.

The module 236 and servers 234 perform the tasks discussed above relative to the processor 116 and the display 340 and servers 238 perform the tasks discussed above relative to the processor 115 though these processors may and often perform additional tasks related to medical information, some examples of which are presented and discussed below and the rest of which are contemplated and achieve the various advantages, results and functions presented herein.

The processor 115, in some embodiments, includes display and visualization 340 executing on one or more servers 238, which may be any suitable computing engine, similar to the servers 232, including but not limited to PCs or servers. The display 340 is used to construct presentation and display information to users, such as the patient's records, billing information, and other types of medical information. The display 340, in some embodiments, also performs processing of some of the functions of the processor 115.

As shown in FIG. 3, the servers 232 are coupled to the module 236 and the servers 234, and to the display 340 and the servers 238 and the module 236 and servers 232 are coupled to the display 340 and the servers 238.

In some embodiments, the interface 113, servers 232, module 236, servers 234, display 340, and servers 238 are remotely located relative to the sources 114 and in some embodiments, remotely located relative to one another. Further, they are considered a part of the Internet cloud where, performing their tasks in a manner known as "cloud-computing". However, other manners of achieving the functions and advantages of the invention, including various other of implementation, not shown in FIG. 3 or other figures herein and/or not discussed are contemplated.

Figure 4:
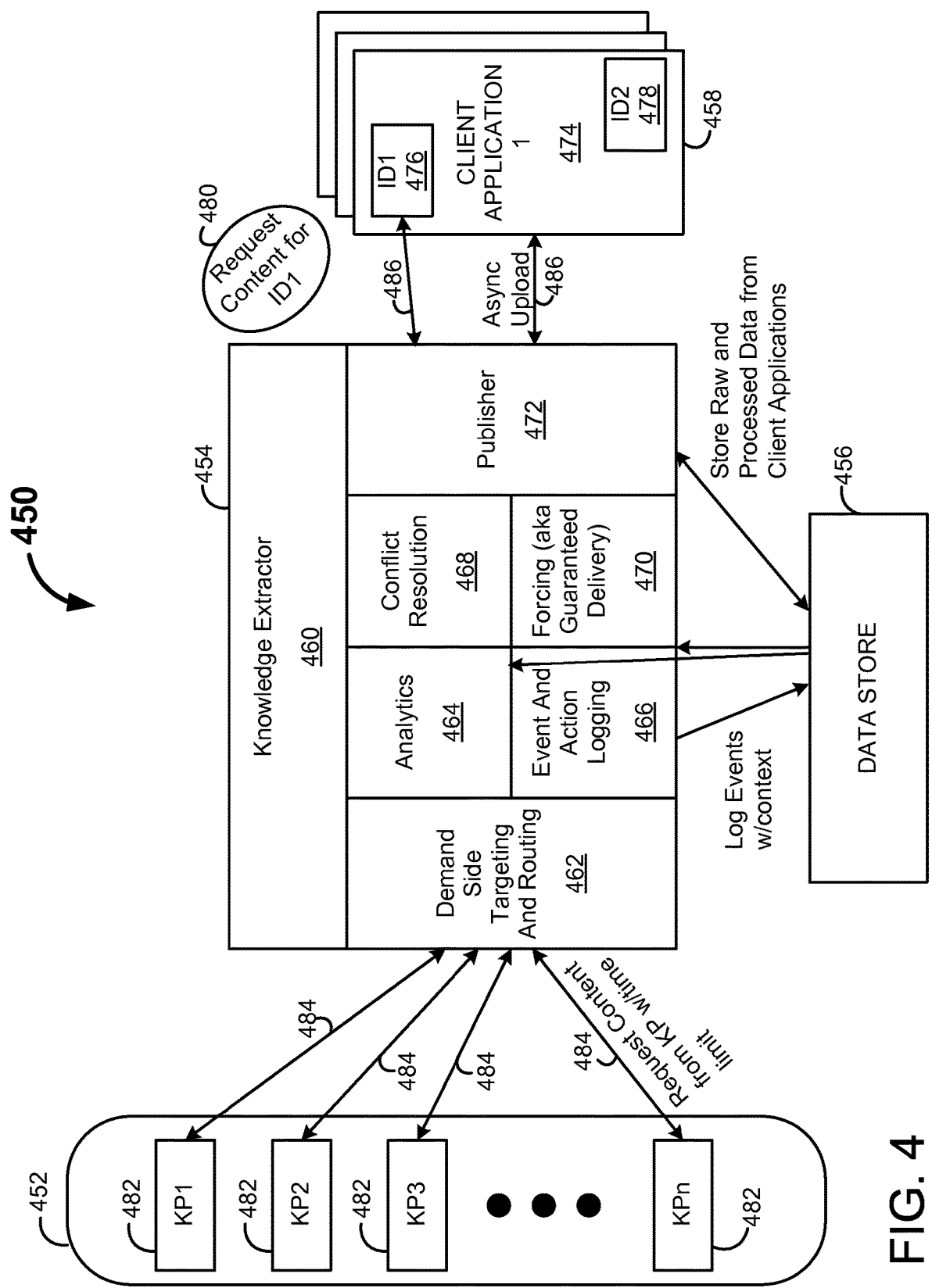
FIG. 4 shows a block diagram of a knowledge extraction system 450, in accordance with an embodiment of the invention.

FIG. 4 shows a block diagram of a knowledge extraction system 450, in accordance with an embodiment of the invention. The system 450 is shown to include a knowledge provider block 452, a knowledge extraction and exchange unit 454, a data store block 456, and a client application block 458. The block 458 executes client or user application 474. The block 452 is analogous to the sources 114 of FIG. 1 and is shown to include a number of knowledge providers 482, with each knowledge provider being analogous to one of the sources discussed above relative to the sources 114. The knowledge extraction and exchange unit 454 is the back-end medical processor, shown in FIGS. 1 and 2. The knowledge extraction and exchange unit 454 is shown to include a demand-side targeting and routing block 462, an analytics block 464, an event and action logging block 466, a conflict resolution block 468, a forcing (or guaranteed delivery) block 470, a publisher block 472, and a knowledge extraction block 460. The block 458 is shown to include one or more impression domain (ID) blocks 476 and 478. While two ID blocks are shown in FIG. 4, it is understood that any number of ID blocks (e.g. problems, procedures, medications, allergies, "did you know?", patient safety items, billing enhancement items, and the like), as required by a user of the system 450, may be employed.

The knowledge extraction and exchange block 454 generally manages the overall process of delivering "content" to the ID blocks 476 and 478 including managing the data store block 456, managing interactions with the knowledge providers 482 and determining which results to present, at 486, to the client application block 458 (which is generally analogous to the front end processor 115 of FIGS. 1 and 2) when a request of "content" is made by one of the ID blocks 476 and 478 and how to rank the requested results. An example of a request is shown at 480 in FIG. 4 where the block 476 is making the request. "Content", as used herein, refers to any information pertinent to the ID, for example a query string, image or hyperlink.

The data store block 456 is generally a storage device or a database storing raw and processed data received from the block 474, through the unit 454. Raw data is data that comes directly from the application 474. Processed data is data that has been processed or optimized for efficient use by knowledge providers. The knowledge extraction and exchange block 454 causes events to be logged with context into the data store block 456 when data is being stored therein. "Events" as used herein refers to user actions such as clicking on a particular content item during a particular search "context".

The knowledge extraction and exchange block 454 communicates with the client application block 458 bi-directionally and typically asynchronously such that when there is a change to the underlying data in the application of the block 458, such as an update to the patient chart, the block 458 sends this updated data to the publisher block 472. The client application block 458 is a client or user application with each of its ID blocks querying for and displaying its particular impression domain content. By way of example only, impression domain content includes items such as problems, procedures, medications, allergies, "did you know?", patient safety items, billing enhancement items, and so on . . . . Each ID presents information to the user that is relevant to the specific patient/user/context at the time the information is displayed. For example, a patient safety ID would present a patient's past history of myocardial infarction to a primary care provider if that event were not noted as structured data the user's EHR application. The publisher block 472 receives content requests from the ID blocks 476 and 478 and in response returns content to be displayed in the blocks 476 and 478. Further, the block 472 receives events (such as clicks) from the ID blocks 476 and 478, receives raw data (such as patient chart updates) from the application block 474, and manages storage of data in the data store block 456 (including event logs, raw client application data and data extracted for the specific needs of the knowledge providers 482 of the block 452).

The demand side targeting and routing block 462 routes content requests to the different knowledge providers 482, received from the client application block 458 by selecting a subset of knowledge providers in real time which it considers most relevant to the current patient/user/context based on criteria provided by the knowledge provider, such as "patient covered by Medicare Advantage", "user is a cardiologist", or "query includes the term EKG", and subsequently receives their responses, through the knowledge provider links 484. In some embodiments, if a knowledge provider 482 with an outstanding content request does not respond within a prescribed amount of time, the request is cancelled.

The conflict resolution block 468 receives content from the demand side targeting and routing block 462 and advantageously determines which of the responses from the knowledge providers 482 to pass to the forcing block 470 and in which rank order. The conflict resolution block 468 uses the content from the ID block 476 or 478 (e.g. patient, user, query) along with analytics on the performance of past knowledge provider results to determine which results are most likely to be useful. For example, if an endocrinologist user always clicks on the hemoglobin al c history after performing a diabetes search, the ID for labs may start automatically displaying the history in response to a diabetes context for that particular user. If enough endocrinologists perform the same action, the ID for labs may start automatically displaying the history for all endocrinologists, whereas such an automatic action might not be performed for general practice users searching for the same diabetic context.

The forcing block 470 receives ranked and selected results from the conflict resolution block 468 and further determine to potentially override the ranking determined by the conflict resolution block 468. For example, if only one result can be displayed in a particular ID block, and it receives a high-value reimbursement result and an important patient safety result, the patient safety result might be given priority over the reimbursement result.

The event and action logging block 466 stores event and action data, such as click-through events in the data store block 456, along with context information (ID context, date, time). Event and action data refers to end user actions e.g. clicking on a particular content that is displayed for more information or history.

The analytics block 464 computes summary statistics for events and actions and places them in the data store block 456 for use by the conflict block 468. End user statistics like click-through rates and dwell times may also be computed by the analytics block 464.

Each of the ID blocks 476 and 478 sends a request to the knowledge extraction and exchange unit 454 asking for certain kinds of result (text, images, links, diagnosis codes) from the knowledge extraction and exchange unit 454. A typical request includes the number of results desired and the context of the request, such as patient identifier, user identifier (and user role, such as specialty, physician or coder or medical assistant, etc) and the search query. The ID block 476 or 478 is responsible for determining how the results are presented to the user of the system 450. For example, when an action is taken, such as a click on a search link, the ID block 476 or 478 also submits this information to the event and action logging block 466.

Each of the knowledge providers 482 computes and returns results that are relevant to a particular ID block request. In some embodiments, the knowledge providers 482 have access to the data store block 456. For example, a knowledge provider might return PubMed articles, up-to-date articles, or best treatment practices that are relevant to the patient/user/context.

Figure 5:
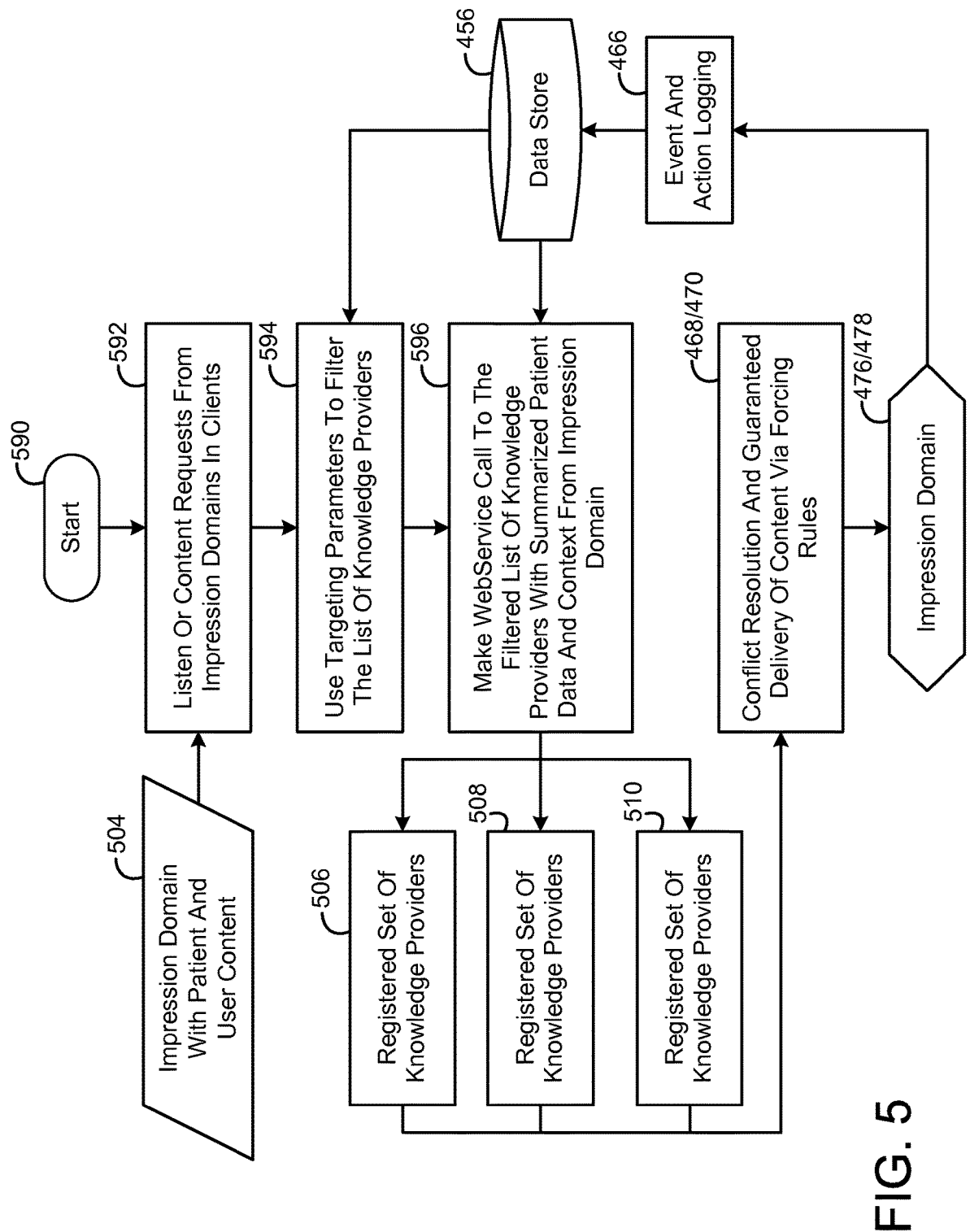
FIG. 5 shows a flow chart of some of the steps performed by the unit 454 of FIG. 4, in conjunction with some of the blocks of FIG. 4 and in accordance with a method of the invention.

FIG. 5 shows a flow chart of some of the steps performed by the knowledge extraction and exchange unit 454 of FIG. 4, in conjunction with some of the blocks of FIG. 4 and in accordance with a method of the invention. The method starts at 590 and at step 592, content requests from the blocks 476 and 478 are awaited by the unit 454. In the meanwhile, at 504, the blocks 476 or 478 may provide the unit 454 with patient and/or user "content" and when they do, the process proceeds to step 594 where targeted parameters are used to narrow the list of knowledge providers 482 in real time based criteria provided by the knowledge provider, such as patient is covered by Medicare Advantage, user is a cardiologist or query includes the term "EKG". Targeted parameters may be received from the block 456, which also provides information for the next step 596. A narrowed list of knowledge providers is referred to herein as "registered set of knowledge providers". At step 596, the knowledge extraction and exchange block 454 makes web-services calls to the narrowed (or "filtered") list of knowledge providers with a summarized patient data and context from the blocks 476 or 478 obtained by knowledge extraction block 460. The summarized patient data is then passed on to the narrowed (or "filtered") list of knowledge providers blocks 506-510. The narrowed (or "filtered") list of knowledge providers 506-510 provide clinically-relevant knowledge to the blocks 468 and 470 where conflict resolution is performed and delivery of content is guaranteed via forcing rules. "Forcing rules" refer to a set of rules that may override decisions made by the conflict resolution module 468.

The outcome of the blocks 468 and 470 is then provided to the block 476 or the block 478, which subsequently captures events and actions and transmits them to the block 466. These events and/or actions are stored, in their raw form, in the block 456.

Figure 6:
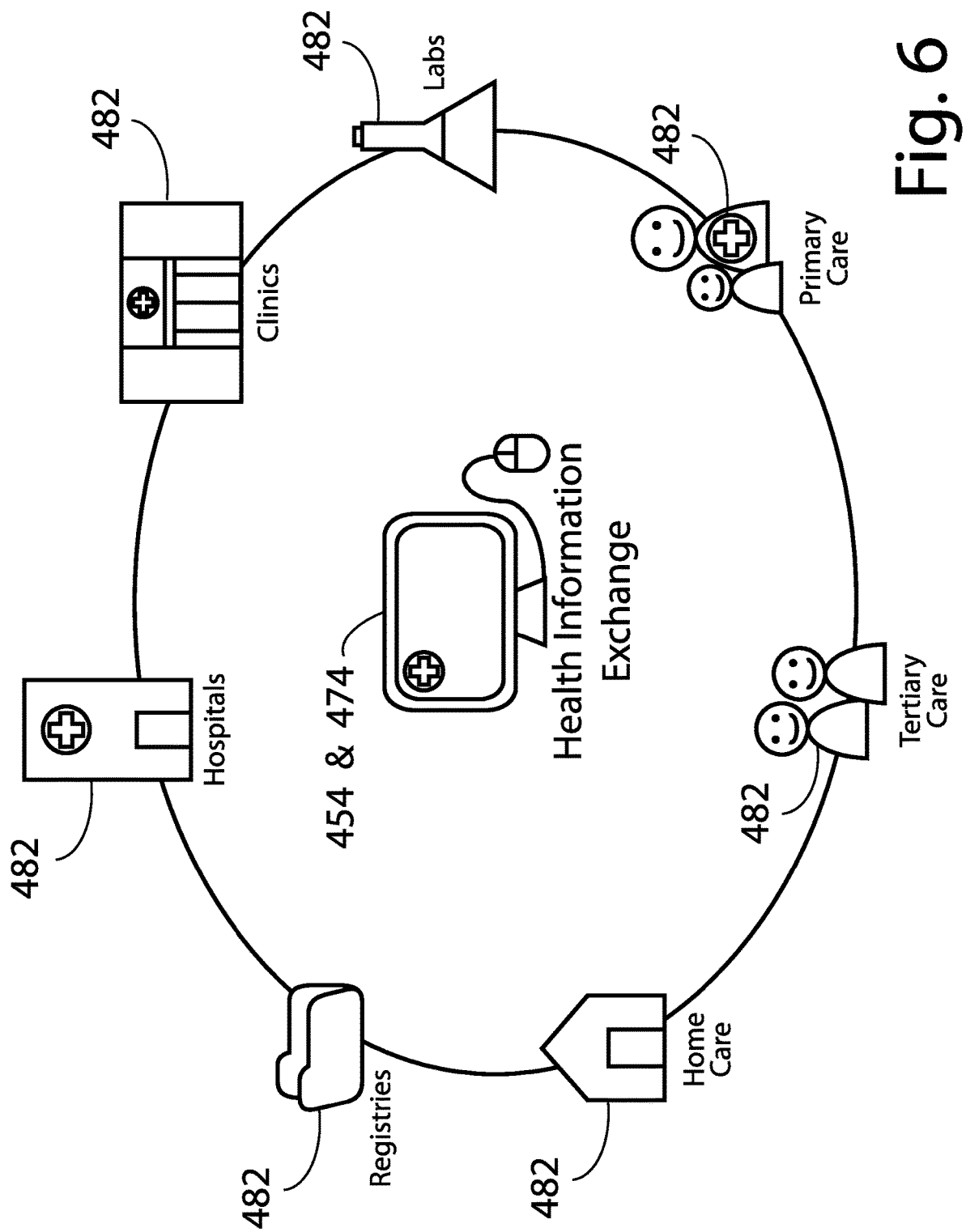
FIG. 6 shows an example of the knowledge extraction and exchange unit 454 and the client application 474 and examples of knowledge providers 482.

FIG. 6 shows an example of the knowledge extraction and exchange unit 454 and the client application 474 and examples of knowledge providers 482. In FIG. 6, the knowledge extraction and exchange unit 454 and the client application 474 are shown to be a mobile device and/or tablet, and the knowledge providers 482 are shown to be a home care facility, a tertiary care facility, a primary care, labs, clinics, hospitals, and registries. It is understood that the knowledge providers 482 of FIG. 6 are merely examples of knowledge providers, in fact, the knowledge providers 482 as well as the knowledge extraction and exchange unit 454 and the client application 474 can be in a field other than the medical field, such as legal services, among others that are contemplated.

Figure 7:
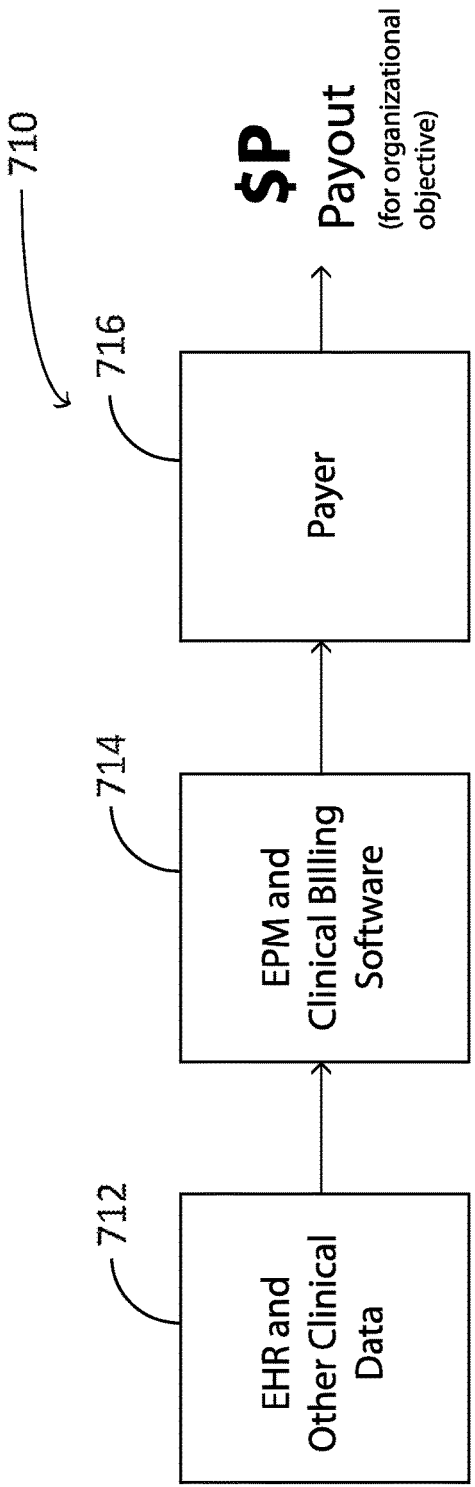
FIGS. 7 and 8 show a model of a healthcare reimbursement system, in accordance with a method and embodiment of the invention.
Figure 8:
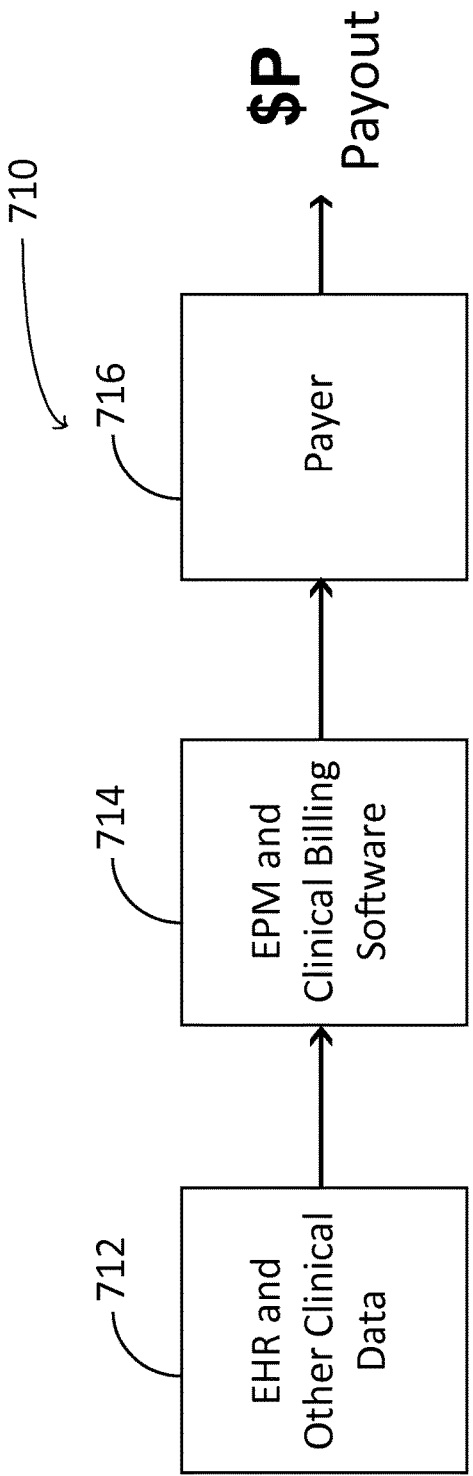

FIGS. 7 and 8 show a model of a healthcare reimbursement system 710, in accordance with a method and embodiment of the invention, consisting of the clinical data 712, billing software 714 and payer 716. In each figure, Eq. (1) is shown to represent the relationship between the organizational objective (P) and efficiency (I) and patient encounter vector [$E_i$; $E_a$]. In Eq. (I), the symbol "*" represents a multiplication operator, the symbols"[ ]" represent a matrix and the symbol ";" represents concatenation.

System for generating prompts for actions that move data from one place to another to achieve organizational objectives (P).

Figure 9:
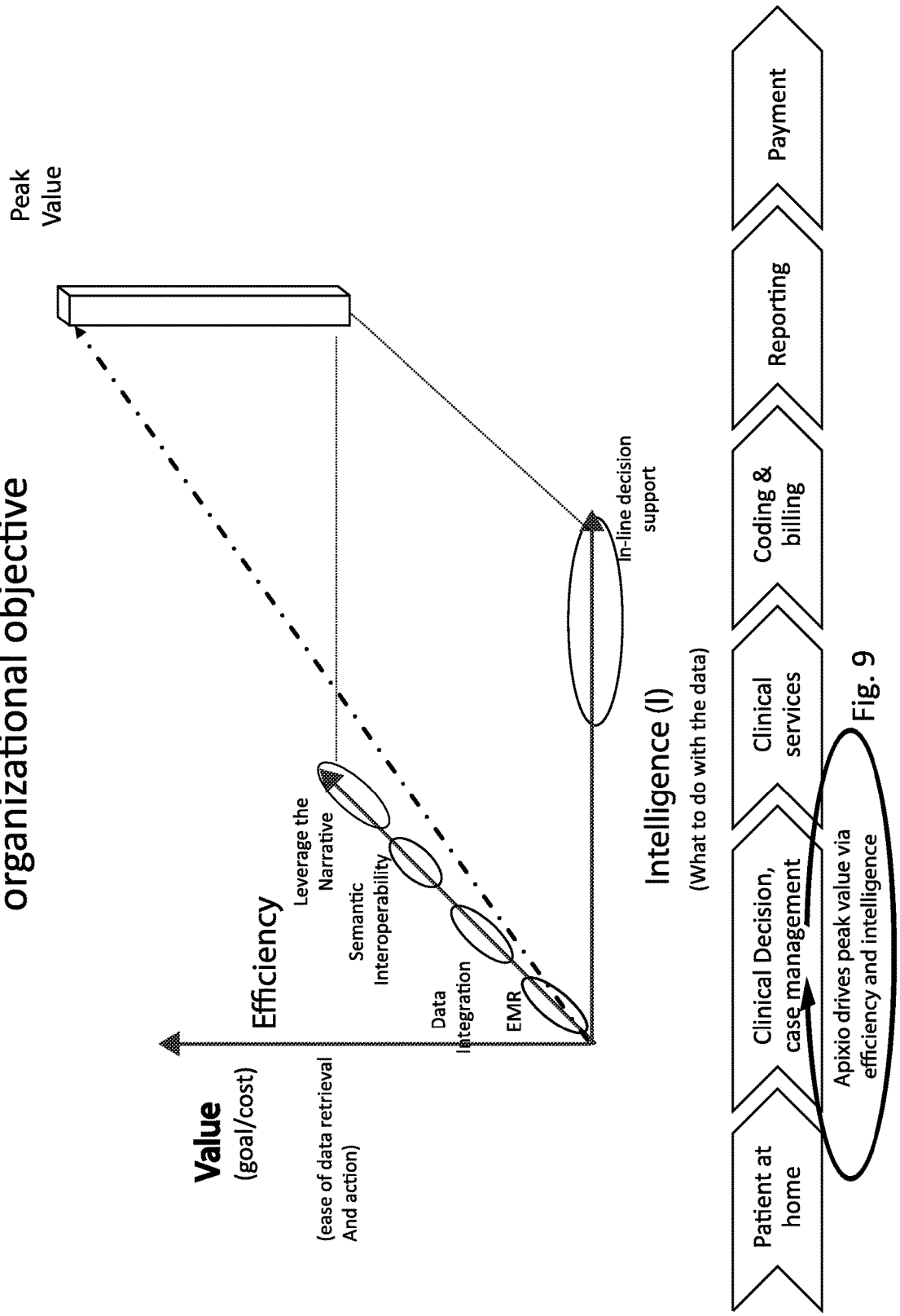
Figure 11:
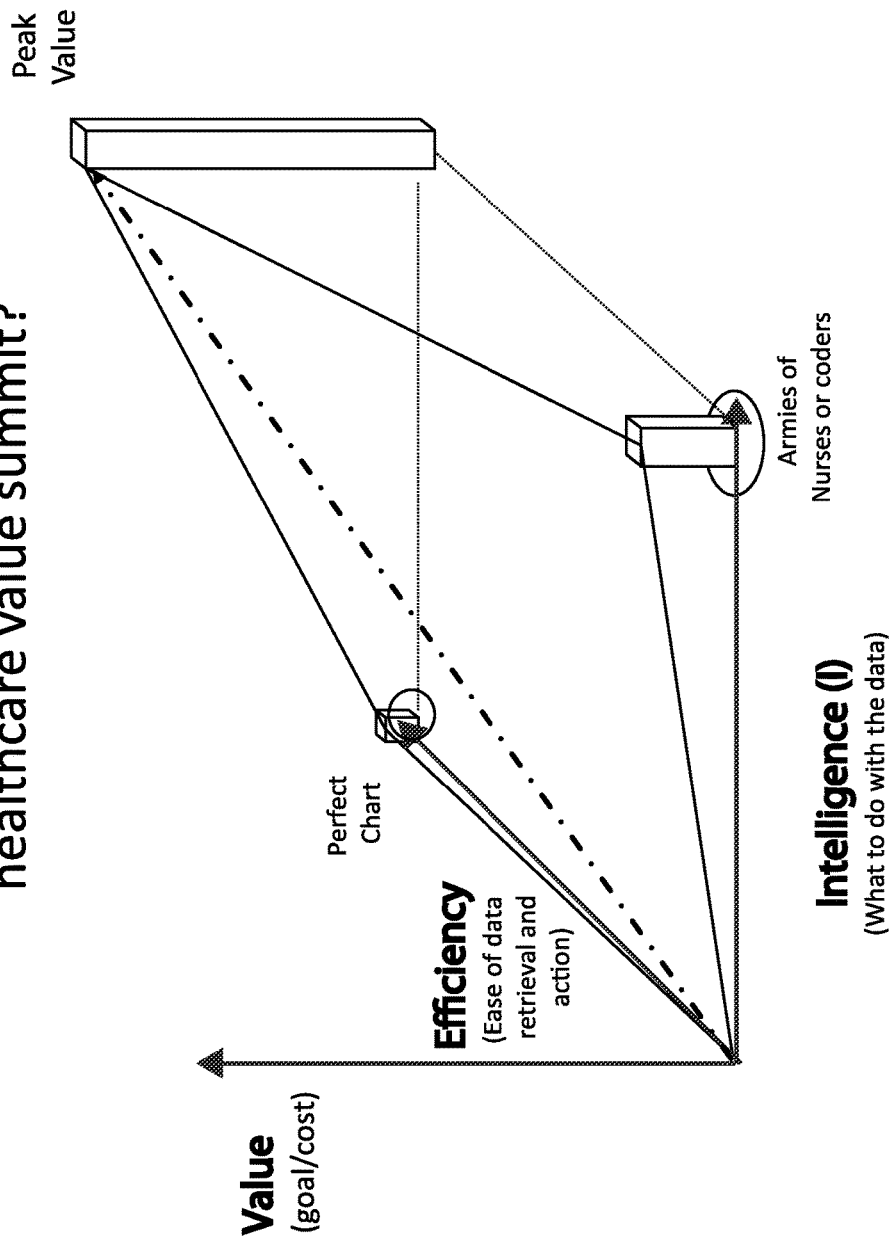
Figure 12:
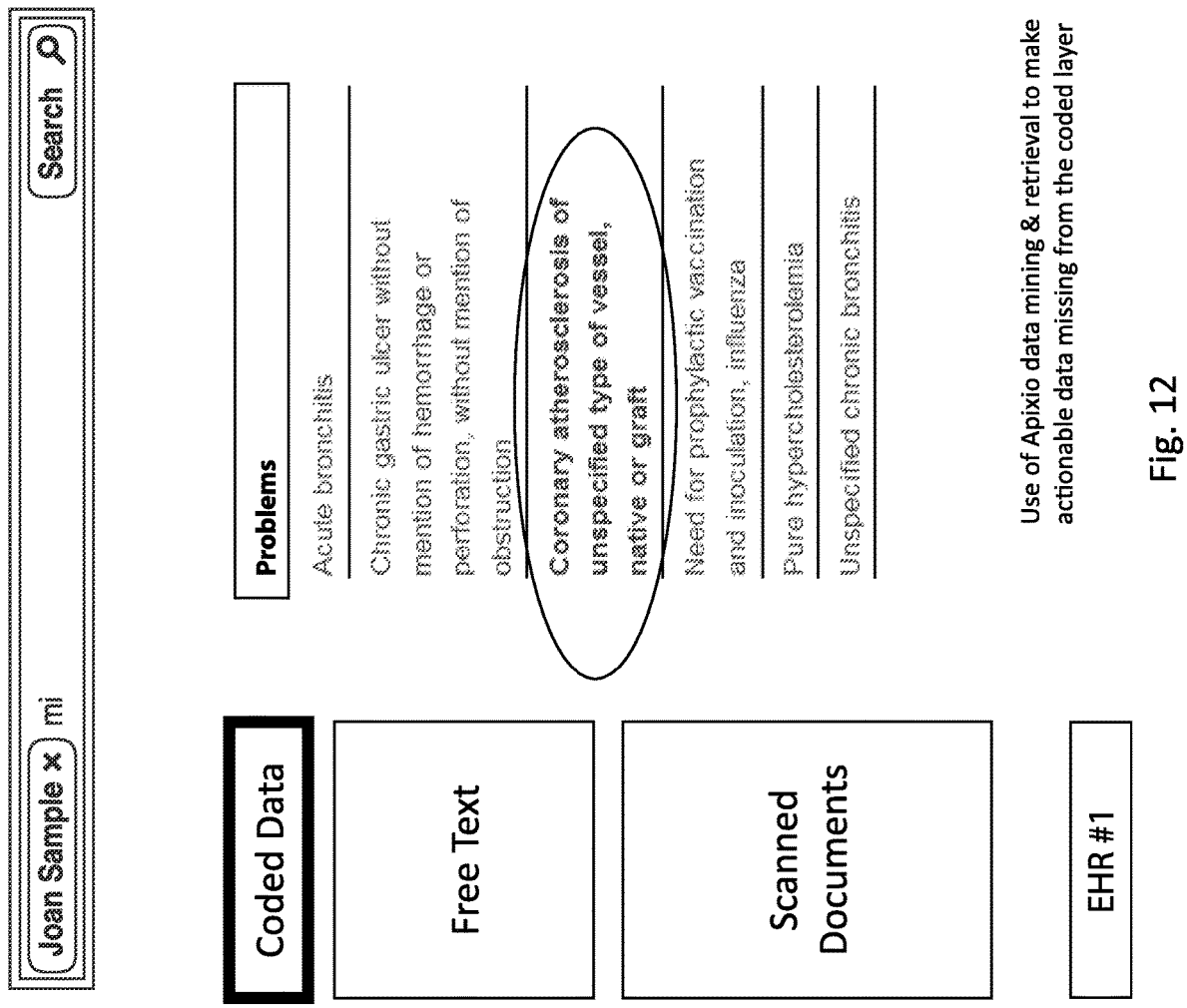
FIGS. 12-18 show an example of a patient/user, Joan Sample, benefiting from the process of extracted information used to determine potential conditions, in accordance with a method of the invention.
Figure 13:
Figure 14:
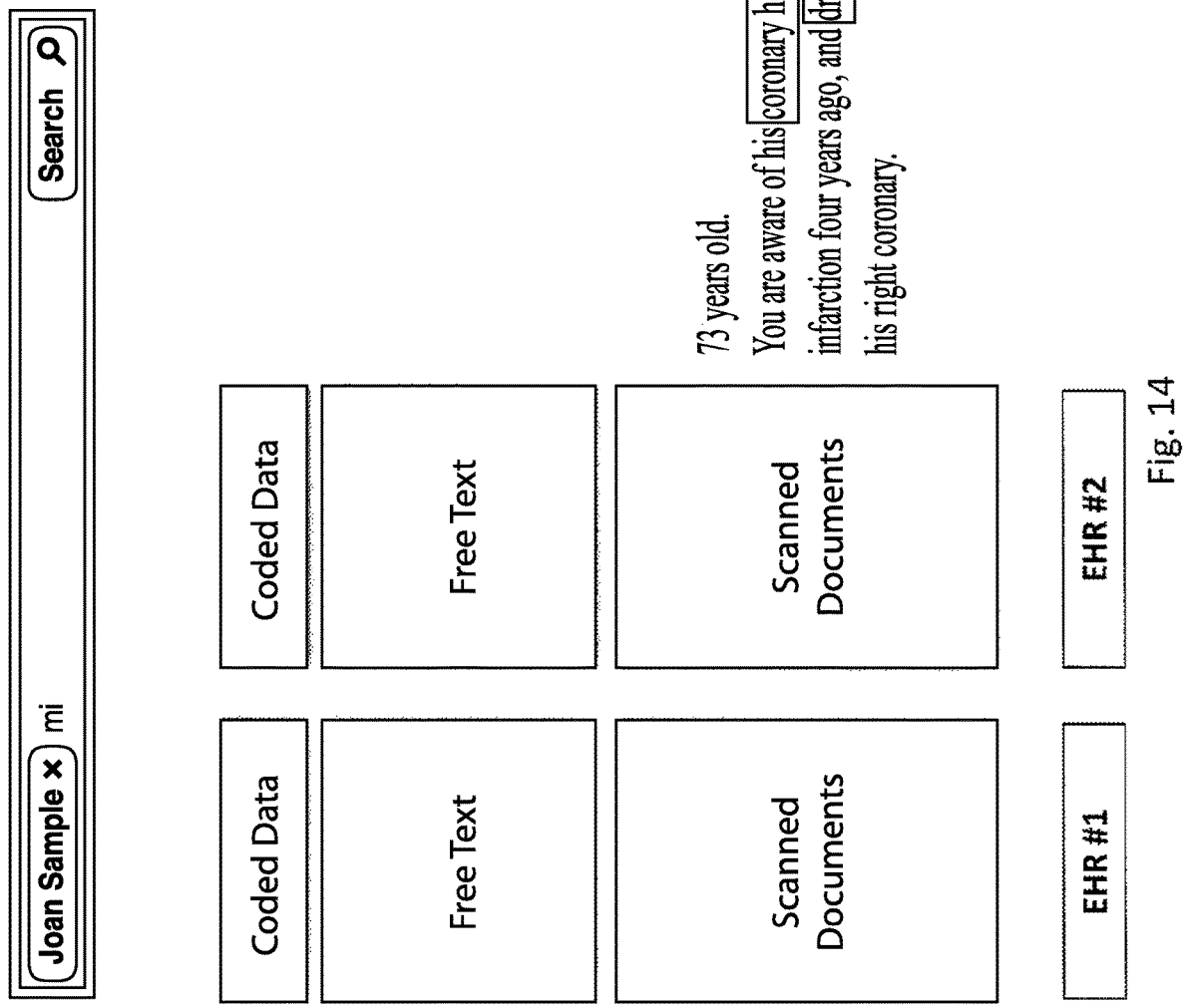
Figure 15:
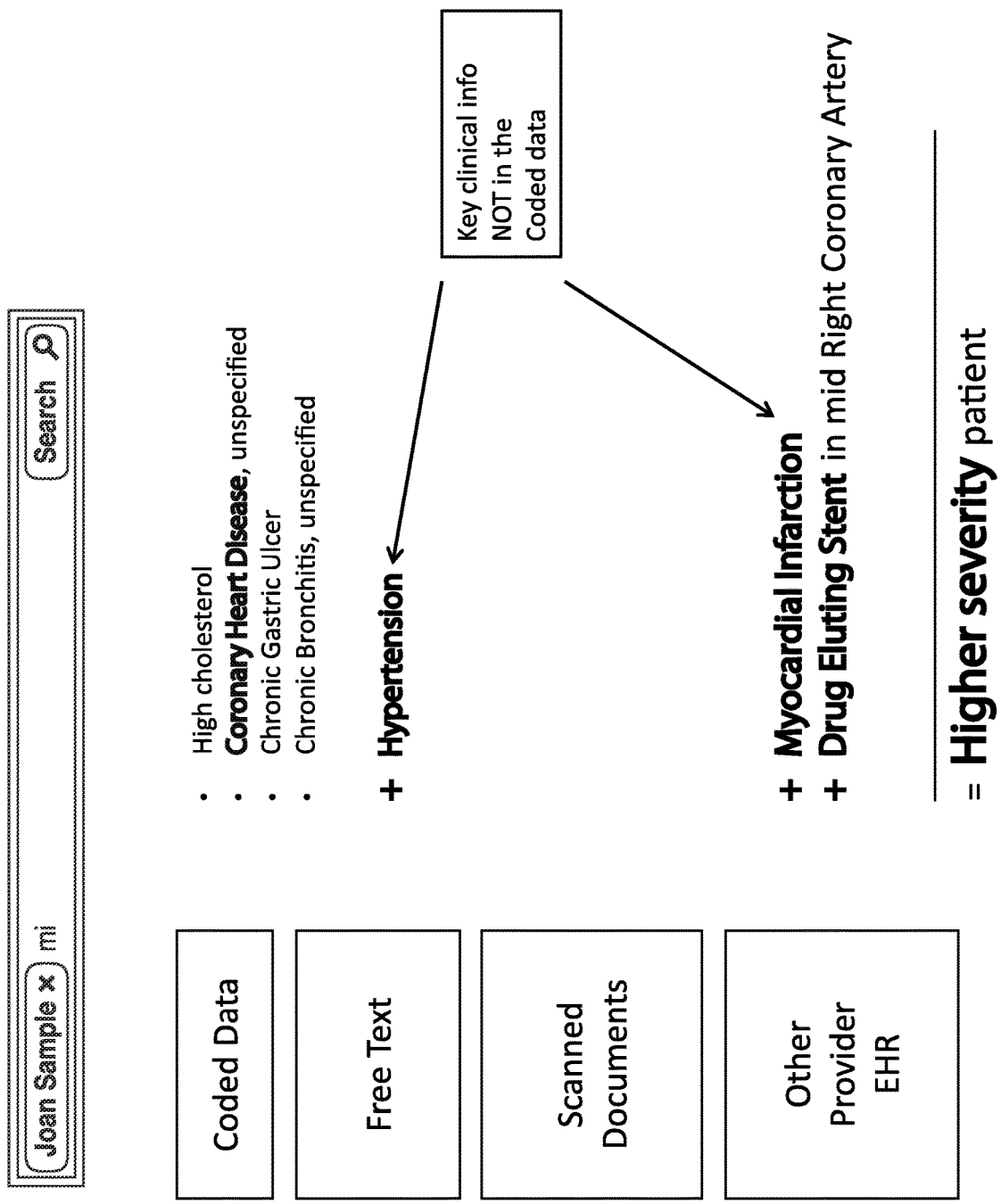
Figure 16:
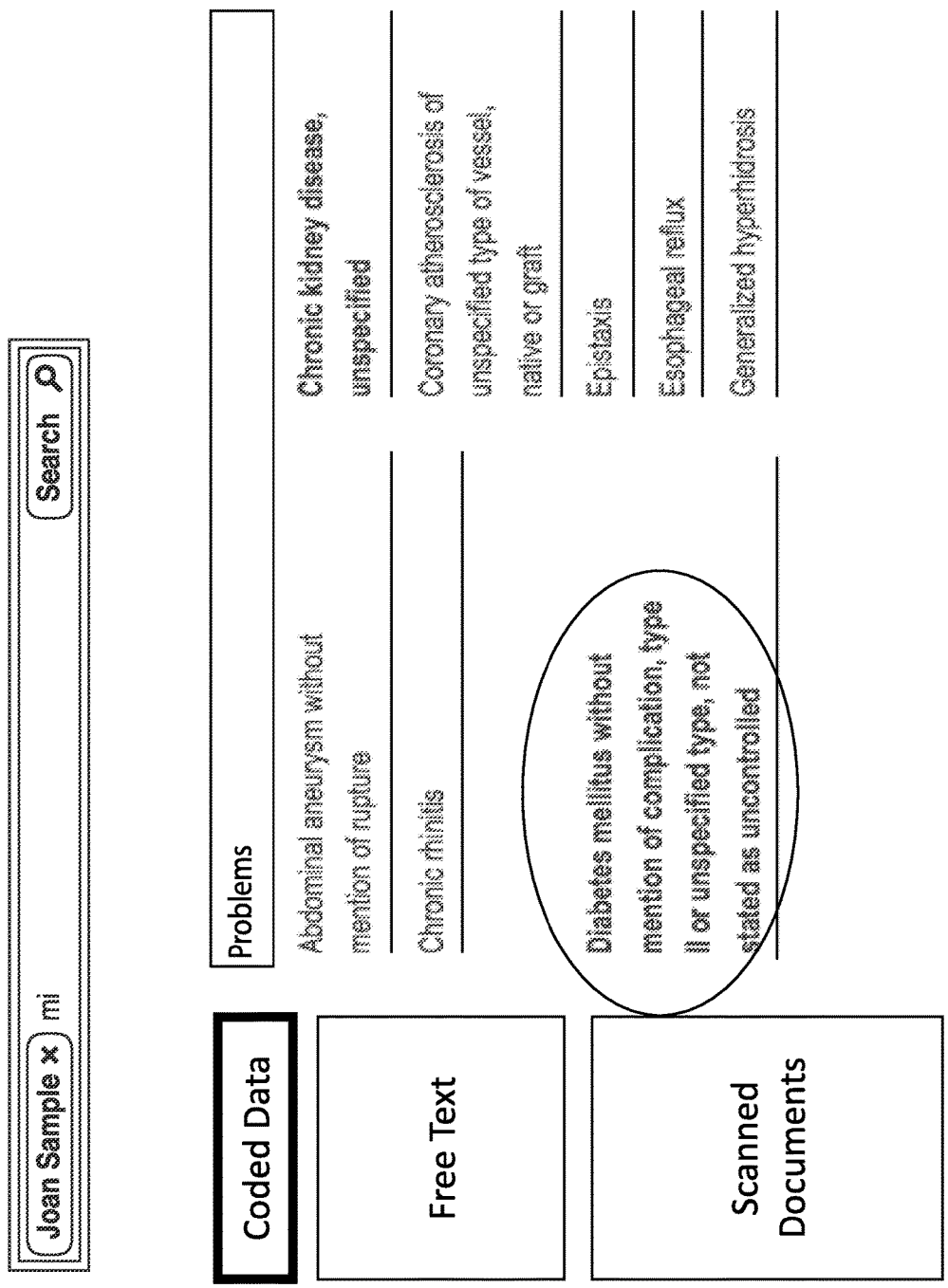
Figure 17:
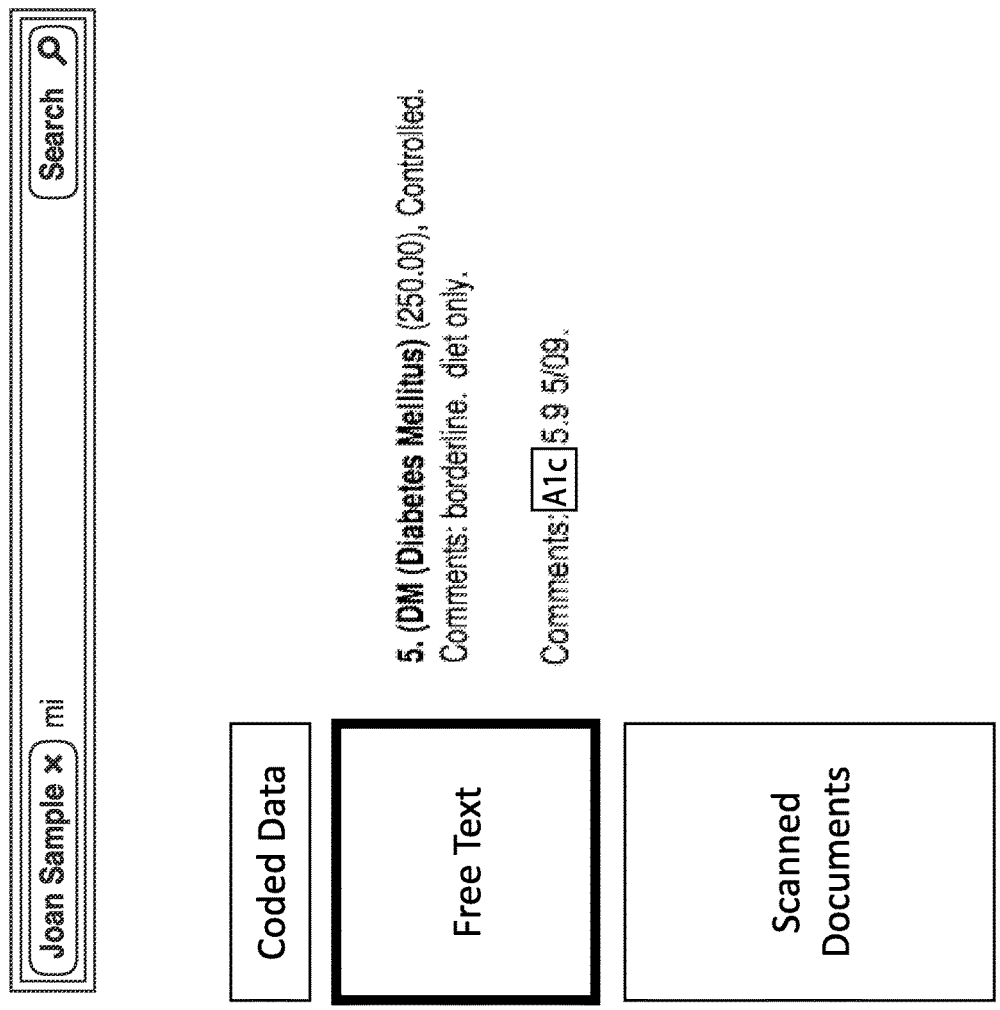
Figure 18:
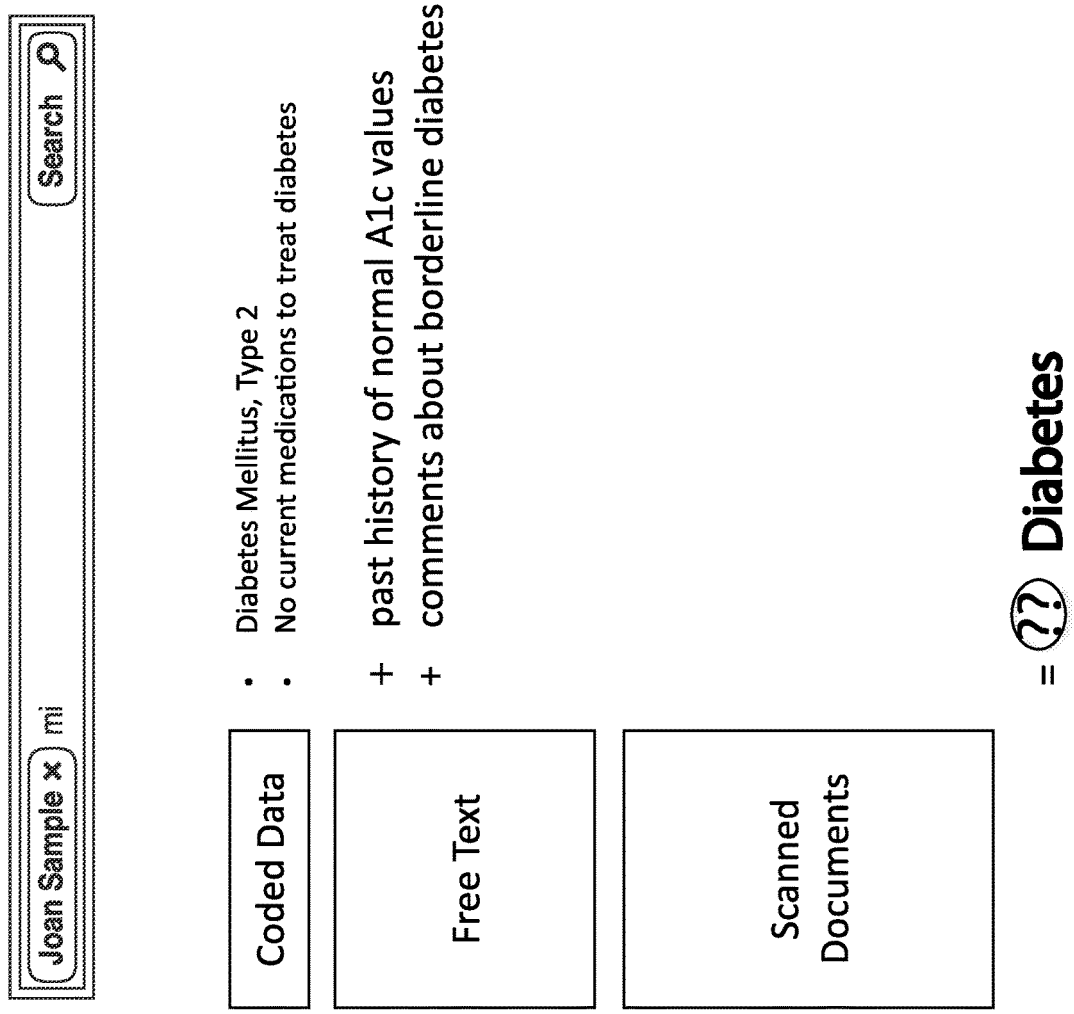

FIGS. 9-11 each show a graph of the intelligence, shown in the x-direction, versus value, shown in the y-direction, of various performance improvements realized using the various methods and embodiments of the invention.

FIGS. 12-18 show an example of a patient/user, Joan Sample, benefiting from the process of extracted information used to determine potential conditions, in accordance with a method of the invention.

Figure 19:
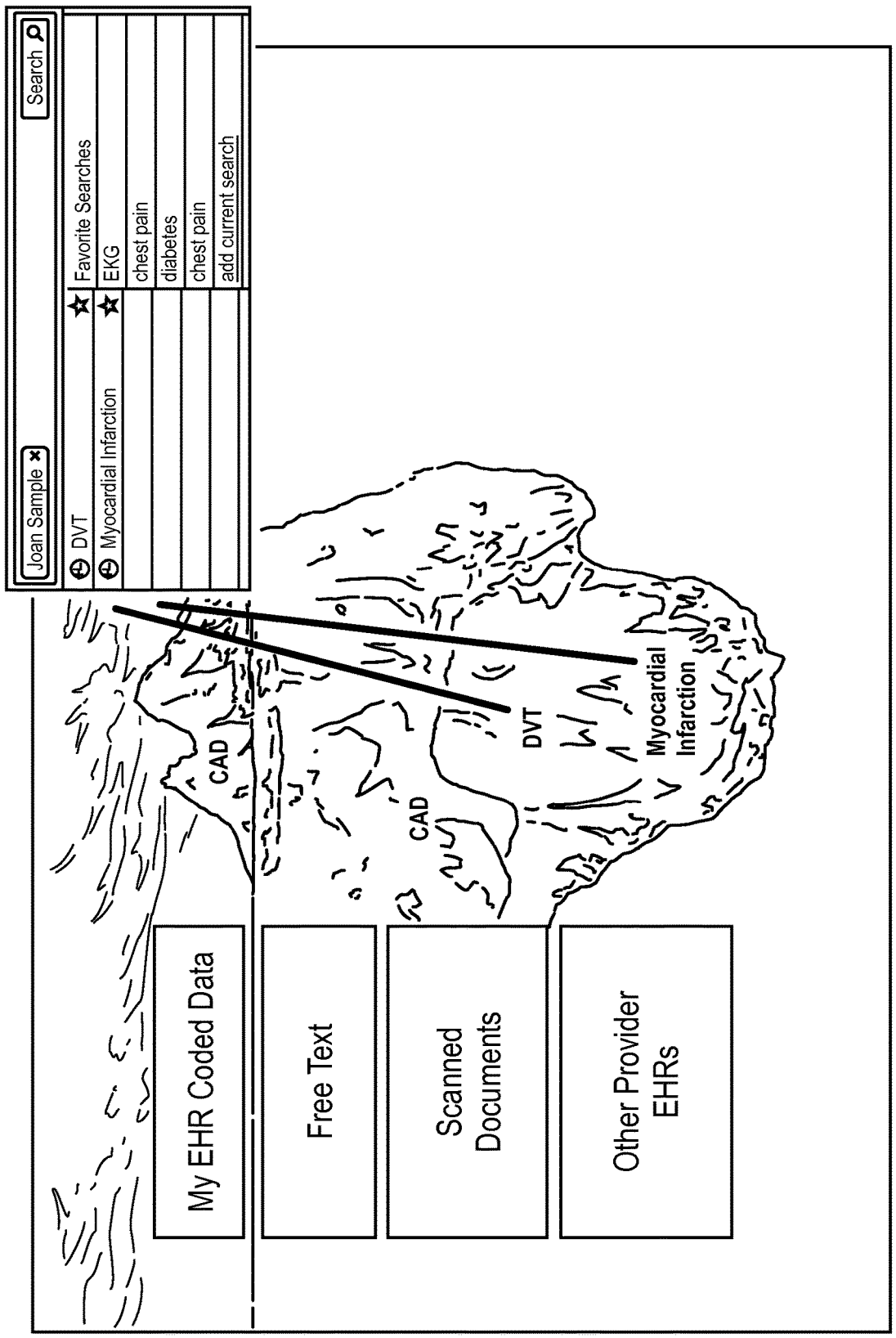
FIG. 19 shows MI and DVT extracted from otherwise hidden information, other provider EHRs and scanned documents, by using the knowledge-based extraction methods and embodiments of the invention.

FIG. 19 shows MI and DVT extracted from otherwise hidden information, other provider EHRs and scanned documents, by using the knowledge-based extraction methods and embodiments of the invention.

Figure 20:
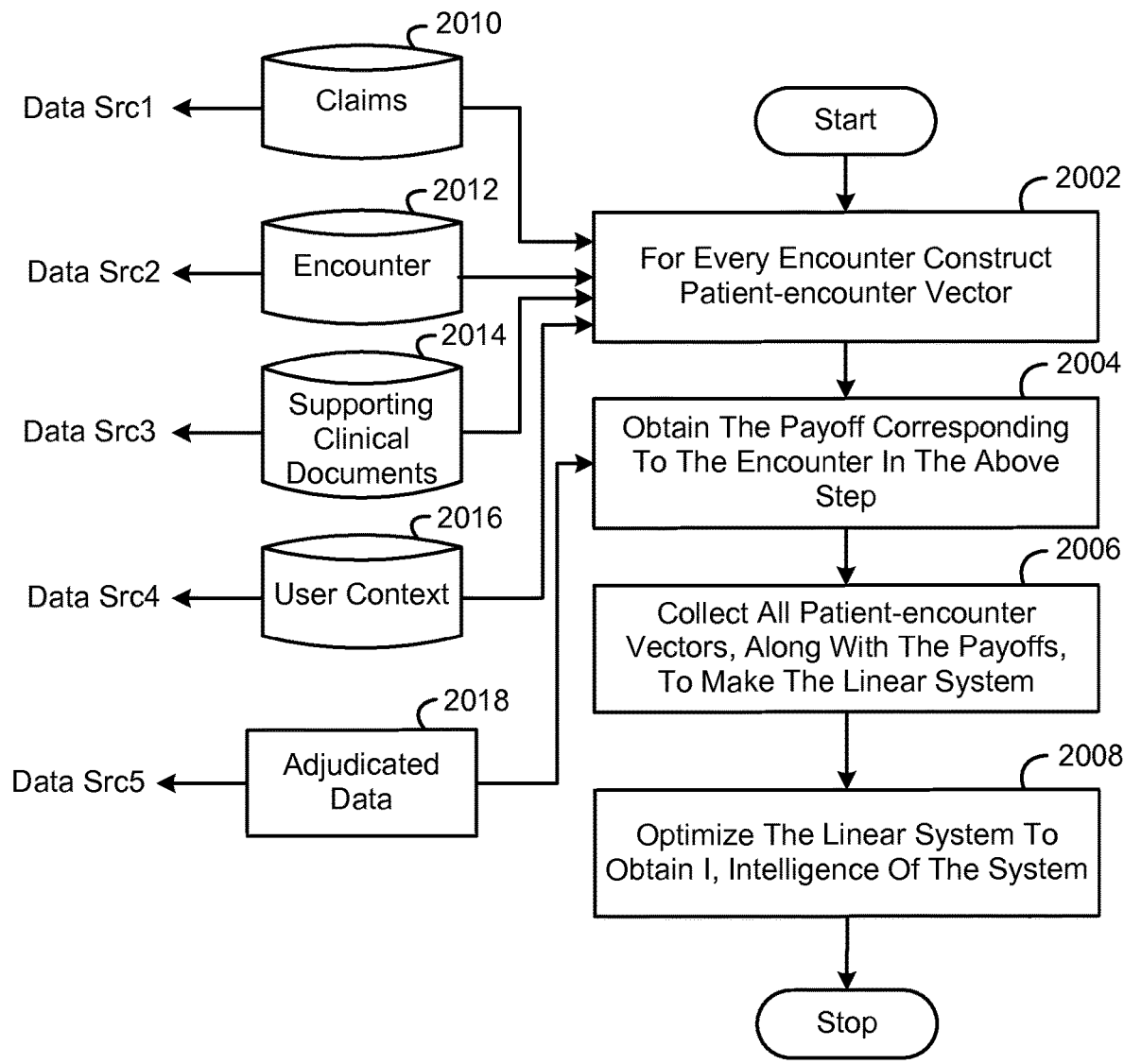
FIG. 20 shows a flow chart of the steps for determining the intelligence (I) of a healthcare system, in accordance with a method of the invention.

FIG. 20 shows a flow chart of the steps for determining the intelligence (I) of a healthcare system, in accordance with a method of the invention. A patient encounter vector is constructed (at 2002) from the claims 2010, encounter data 2012, clinical documents 2014 and user context data 2016. The payoff corresponding to the encounter is obtained (at 2004) using adjudicated data 2018. All patient encounter vectors are collected, along with the payoffs to make a linear system (at 2006), which is optimized to obtain the intelligence (I) of the system (at 2008).

Figure 21:
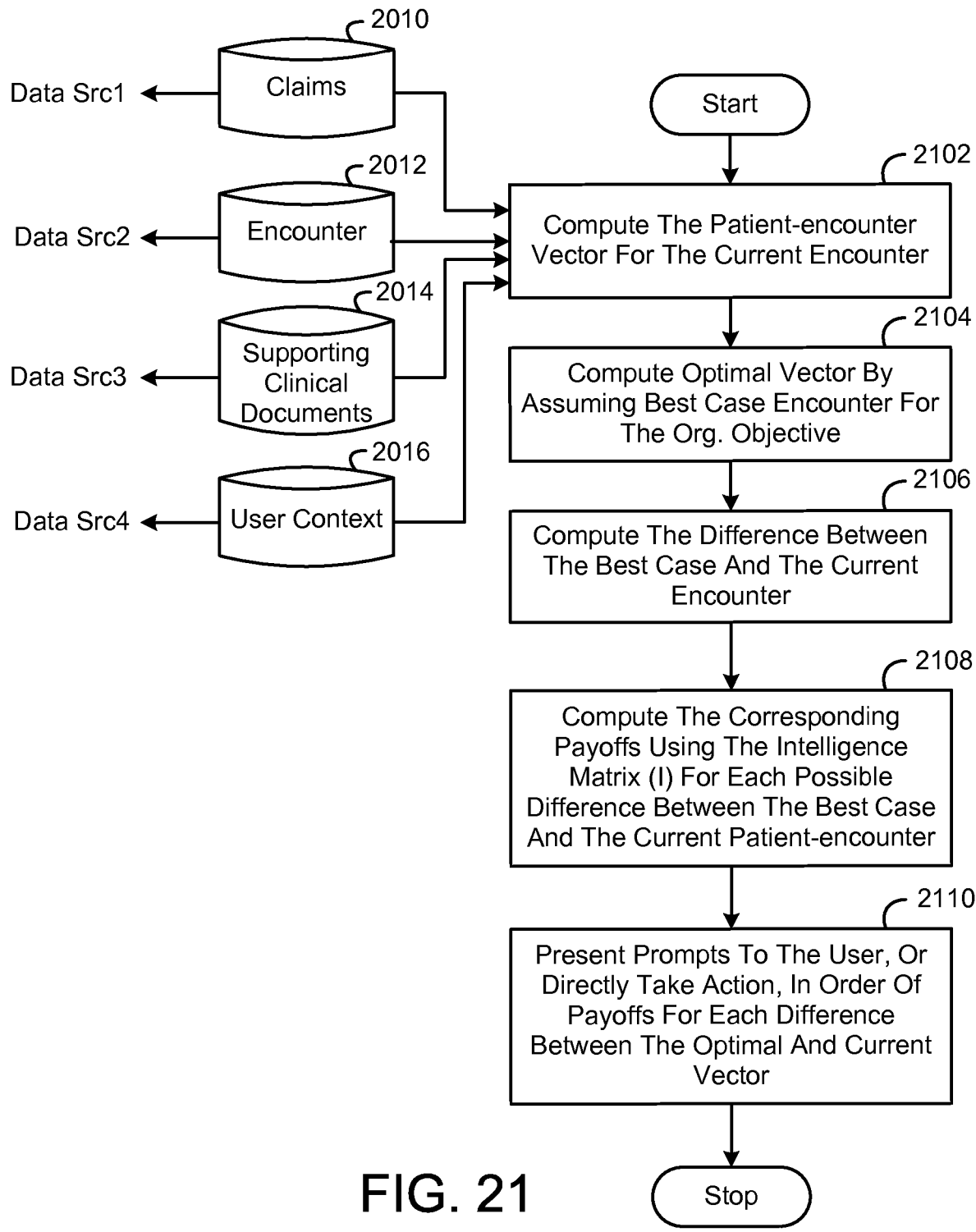
FIG. 21 shows a flow chart of the steps for application of hierarchal condition categories Hierarchical Condition Category (HCC), in accordance with a method of the invention.

FIG. 21 shows a flow chart of the steps for application of hierarchal condition categories (HCC), in accordance with a method of the invention.

In FIG. 21, the data "src" or sources shown on the left side of the page are data that is provided by various sources, such as sources 2014, in the form of claims 2010, encounter 2012, supporting clinical documents 2014, and user context 2016. In FIG. 20, the "I" or intelligence of the Eq. (1) of FIGS. 7 and 8, is determined and in this respect, show further details of a knowledge provider 482.

The steps of FIG. 21 are for application of hierarchal condition categories (HCC) and advantageously identify the first order HCC gap alerts. A patient encounter vector is constructed (at 2102). The optimal vector is computed by assuming best case encounter for the organization's objective (at 2104). The difference between the best case and current encounter is computed (at 2106). The corresponding payoffs are computed using the intelligence matrix for each possible difference between the best case and current encounter is computed (at 2108). Prompts are presented to the user, or action is directly taken, in order of payoffs (at 2110).

Figure 22:
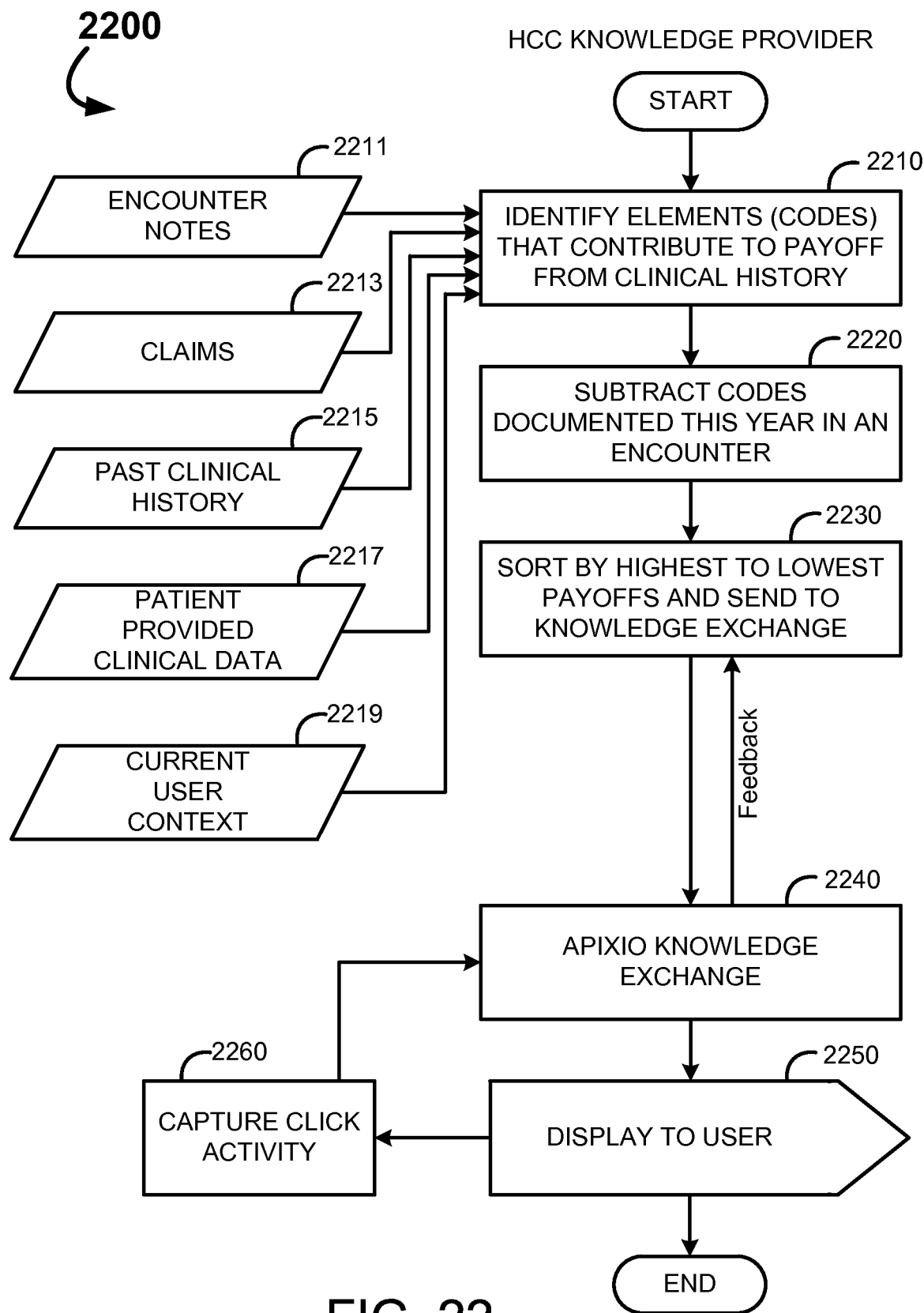
FIG. 22 shows a flow chart of the steps performed in extracting relevant information from a patient's clinical history for the purpose of identifying information that will impact the reimbursement paid to a healthcare organization for the management of a patient.

FIG. 22 includes an exemplary flow chart showing the steps performed in extracting relevant information from a patient's clinical history for the purpose of identifying information that will impact the reimbursement paid to a healthcare organization for the management of a patient. In this example, a HCC Knowledge Provider 2200 mines the patient problems and diagnoses that will impact the reimbursement (via HCC coding) paid to under a plan (e.g., Medicare Advantage) by a healthcare payer (e.g., Medicare). In step 2210, non-negated instances of diagnoses in the patient history (coded, textual, image, etc.) are identified and associated with related diagnoses that impact reimbursement, using encounter notes 2211, claims 2213, past clinical history 2215, patient provided clinical data 2217 and current user context 2219. All concepts that have already been submitted to the health plan during the relevant reimbursement period (for example, one calendar year) are removed from the list of retrieved concepts (step 2220).

In step 2230, the list are arranged and ranked in order based on the expected payout for the concept (this can be based on a lookup table or the Clinical Knowledge Exchange model of the healthcare system) and the click-through rate of the concept (computed using the click history of the concept, including the user context, query and patient history itself). The resulting concepts with rankings above a given threshold will be submitted to the Knowledge Exchange 2240 for possible presentation to the user (step 2230). The Knowledge Exchange 2240 records whether or not the concept is presented to the user and if so, whether or not it was clicked. Additional events may be recorded along with the click event (at 2360). These elements, e.g., codes, can be stored by the Knowledge Exchange 2240 and passed back to the Knowledge Provider 2200 for use in future rankings.

The Clinical Knowledge Exchange model of a healthcare system is a set of mathematical representations of how clinical and other information flows in a healthcare system. Each model is conditioned on a particular outcome that is relevant to the operations of the healthcare system. The Clinical Knowledge Exchange model has been described in detail above and as illustrated by in FIGS. 4-6.

Figure 23:
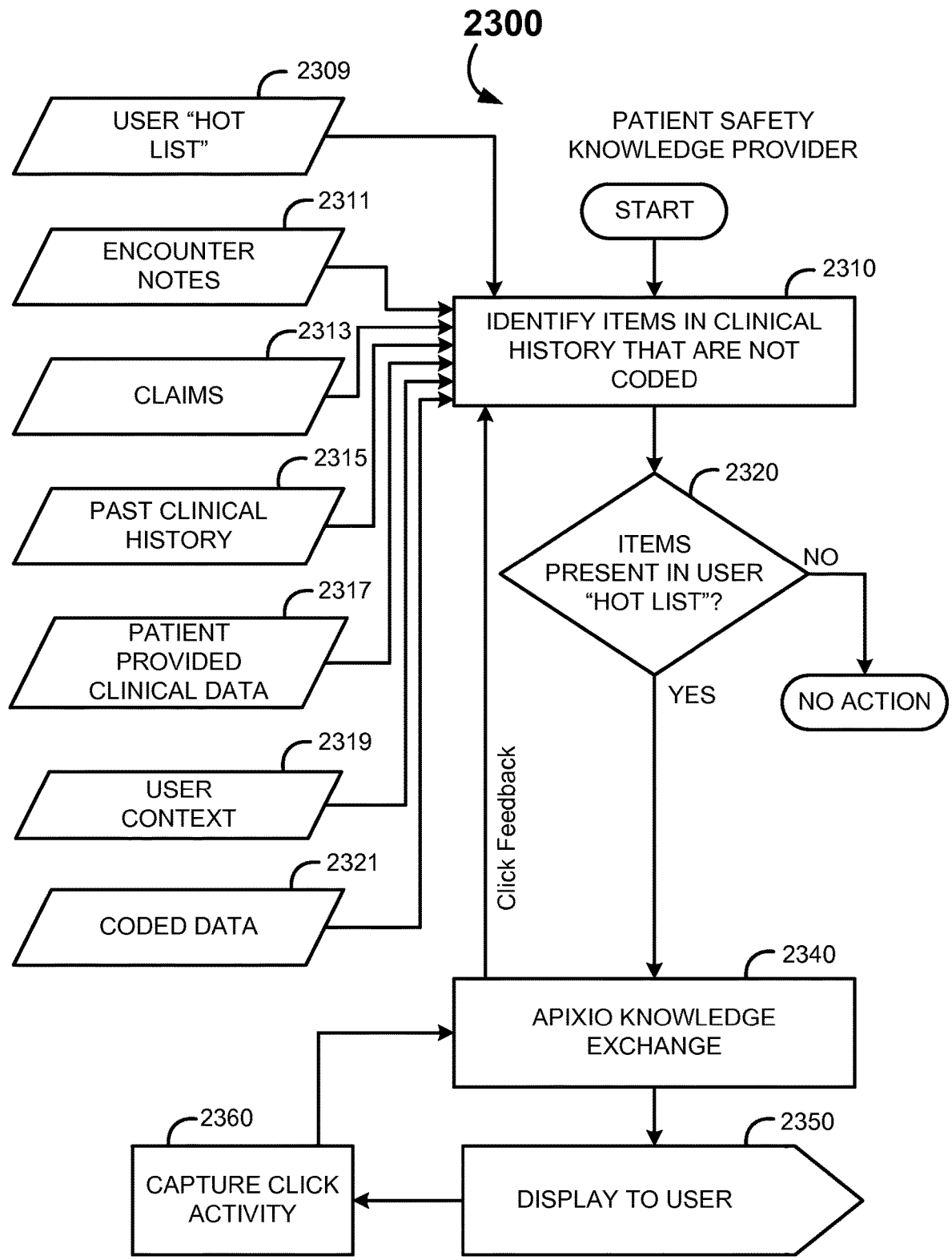
FIG. 23 shows a flow chart of the steps performed in extracting critical information in the records of a patient's history, for display and other use, and particularly for improving patient safety by avoiding missing relevant patient history.

FIG. 23 includes another exemplary flow chart showing the steps performed in extracting critical information in the records of a patient's history, for display and other use, and particularly for improving patient safety by avoiding missing relevant patient history. In this example, a Patient Safety Knowledge Provider 2300 mines the patient's clinical history for non-negated medical concepts that are relevant to patient safety. In step 2310, the process identifies all non-negated instances of medical concepts (such as diagnoses, medications, procedures, measurements, allergies, symptoms, treatments, etc.) in the patient history (coded, textual, image, etc.) including user 'hot list' 2309, encounter notes 2311, claims 2313, past clinical history 2315, patient provided clinical data 2317, user context 2319 and coded data 2321. In one representation, all concepts that are present in the current coded problem list in the user's local EHR are removed from the list of retrieved concepts. The process then arranges the list in rank order based on a number of factors, including degree of medical association (see below), potential severity or risk to patient and the clickthrough rate of the concept (computed using the click history of the concept, including the user context, query and patient history itself). The resulting concepts with rankings above a given threshold will be submitted to the Knowledge Exchange 2340 for possible presentation to the user (at 2350). As described above, the Knowledge Exchange 2340 records whether or not the concept is presented to the user and if so, whether or not it was clicked. Additional events may be recorded along with the click event (at 2360). All of these items are then stored by the Knowledge Exchange 2340 and passed back to the Knowledge Provider 2300 for use in future rankings.

In this embodiment, as illustrated by step 2320, concepts that are included on a "hot list" provided by the user are considered for presentation, allowing each user to define a customized set of relevant concepts.

In some embodiments, problems and medications that have been extracted from the patient history are checked in subsets (pairs, triples, etc.) against known possible risks and interactions as part of the ranking step. The resulting concepts that are submitted to the Knowledge Exchange 2340 for possible presentation then represent potential contraindications, interactions and other risks to the patient's safety.

Figure 24A:
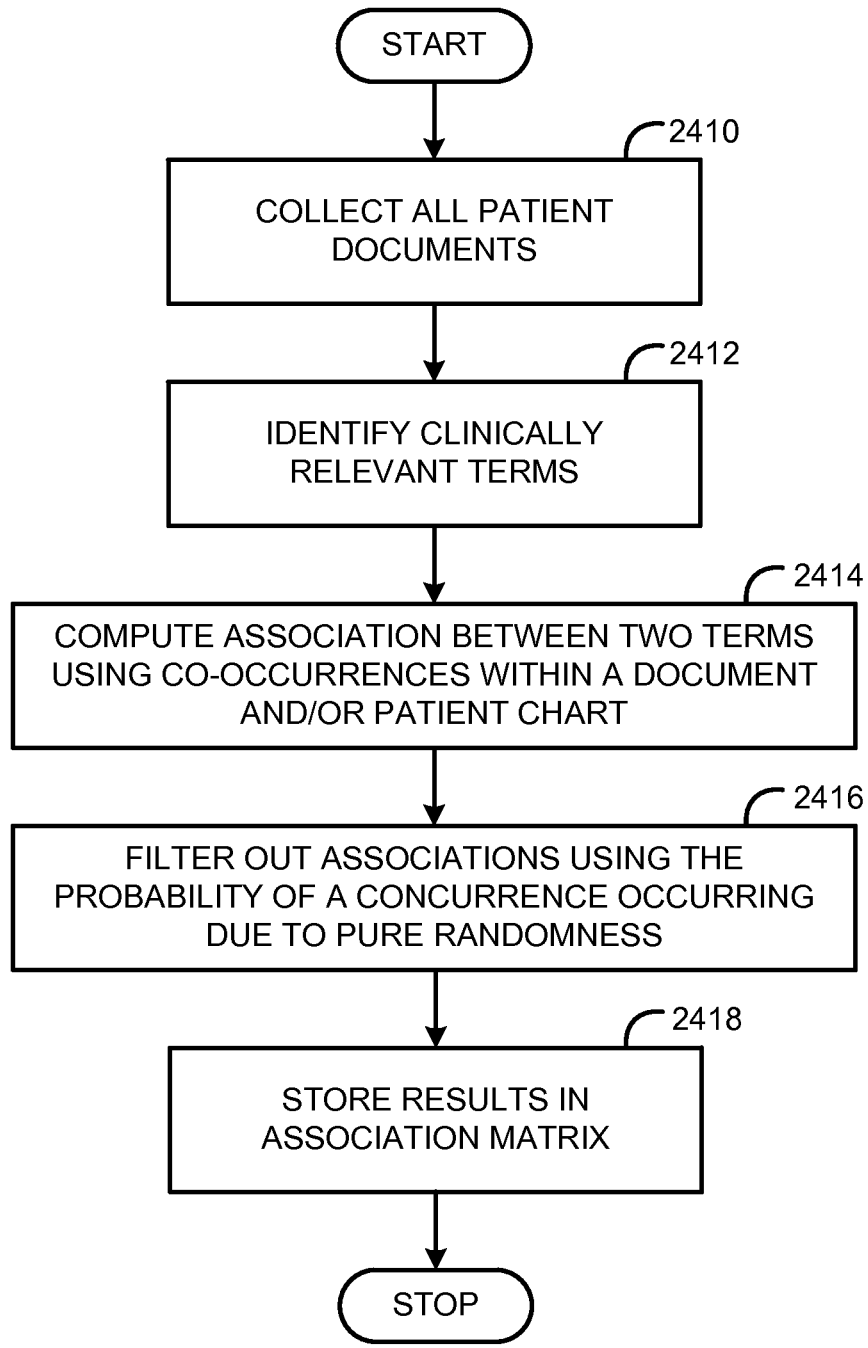
FIGS. 24a and 24b show a flow chart of the steps performed in computing concept associations in building an association matrix and related results, based on certain criteria or parameter, such as but not limited to, recency, risk, strength of association, and user content. See below for detailed descriptions.
Figure 24B:
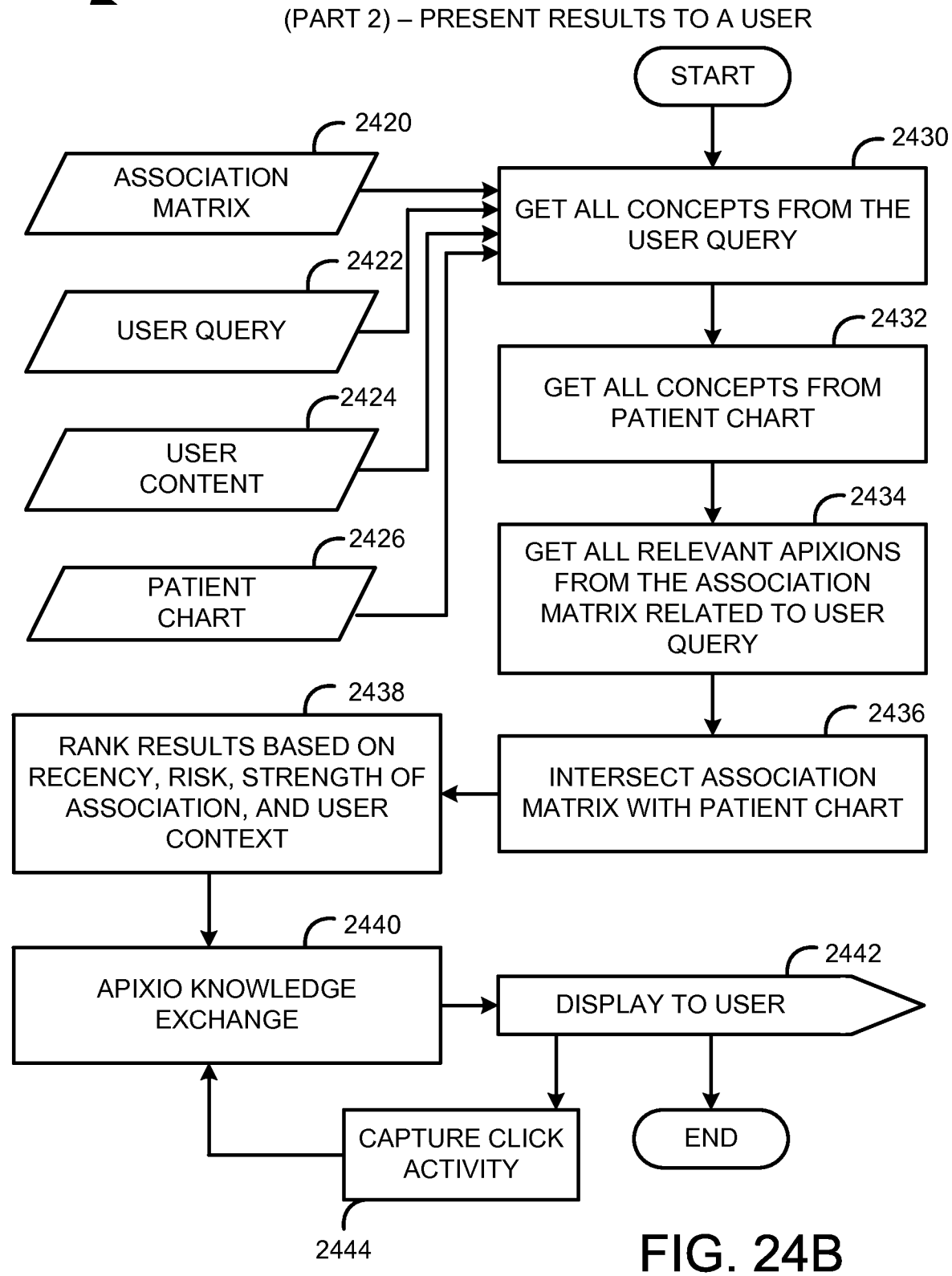

FIGS. 24a and 24b are flow charts showing exemplary steps performed in computing concept associations in building an association matrix and related results, based on certain criteria or parameter, such as but not limited to, recency, risk, strength of association, and user content. See below for detailed descriptions.

FIG. 24a shows a flow chart 2400a of the steps taken to automatically compute associated clinical concepts by mining patient charts in the aggregate. Aggregating patient information across a large number of patients, we collect all electronic documents, scanned documents and other structured data available from EHR and other clinical information systems to build a comprehensive patient chart, for each patient.

For each patient, as shown in steps 2410 and 2412, pairs and triples of clinical concepts are generated and identified by their code in a standardized coding system such as SNOMED, ICD-9, ICD-10, LOINC, and HCPCS. The triples and pairs are collected from all the patient charts to compute their co-occurrence within a patient chart.

Based on the co-occurrence, the degree of correlation between any two concepts is computed (step 2414). The pair-wise associations are then filtered by comparing (taking the ratio of) the probability of the association as observed in the data with the probability of association due to randomness (see step 2416). This ratio is then used to filter out spurious associations from real associations obtained from the data.

In step 2418, these associations are stored in a large matrix (the association matrix) that can be accessed to obtain the degree of association between any two concepts. As all the associations are computed using aggregate patient data, no PHI is exposed when the associations are computed.

FIG. 24b shows a flow chart 2400b of the steps performed for a Related Results Knowledge Provider. When a user types in a query to search a patient chart, the related results knowledge provider extracts all the clinical concepts within a user query 2422, the concepts identified by standard coding systems such as SNOMED, ICD-9, ICD-1 0, LOINC, and HCPCS (see step 2430) from the association matrix 2420, user content 2424 and patient chart 2426. The related results knowledge provider also extracts all the clinical concepts within a patient's chart (see step 2432).

In steps 2434 and 2436, using the association matrix computed using the method described above, the Related Results Knowledge Provider generates a candidate list of related items within the patient chart that are related to the user query and that might be of interest to the user who provided the original query to the system.

In step 2438, this candidate list is then ranked and sorted according to the following exemplary criteria:
1. Recency of the related item in the patient's chart
2. Risk to the patient of the related item in the patients chart
3. Specialty of the user
4. The source of the data (for example, user's local EHR, external EHR, community HIE, external PACS system, user-generated data, etc.)
5. Strength of association between the related concepts and the user query.

The related results are provided to the user within their workflow (e.g.: EHR, billing system, case management system, etc.) using Clinical Knowledge Exchange 2440 (see steps 2440, 2442, 2444).

Figure 25:
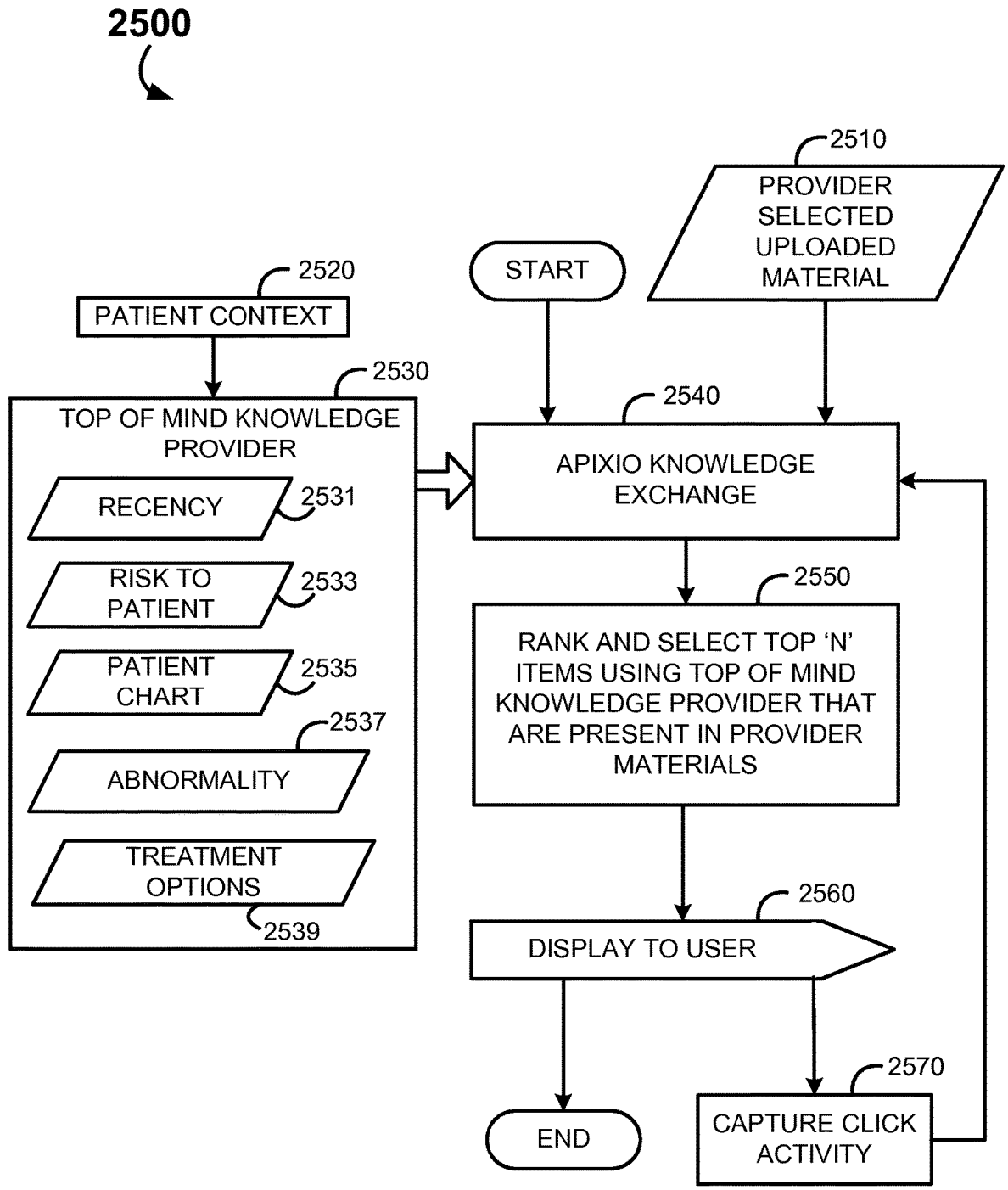
FIG. 25 shows a flow chart of the process for Top of Mind Knowledge Provider.
Figure 27:

FIG. 25 is a flow chart 2500 showing an exemplary process for a Top of Mind Knowledge Provider 2530. The Top of Mind Knowledge Provider 2530, is a specific knowledge provider, that can be integrated into patient portals, mobile devices, mobile and web based applications targeted at the patient and user interfaces/portals (e.g. My Apixio). The Top of Mind Knowledge Provider 2530 receives patient context data 2520 and includes data related to recency 2531, risk to patient 2533, patient chart 2535, abnormality 2537 and treatment options 2539.

In steps 2510, 2540 and 2550, the Top of Mind knowledge provider 2530 mines the contents of a patient's chart along with other clinically relevant sources of material either from the web, based on provider specific preferences and patient's browsing and search history to suggest search terms that can direct the patient to learn more about specific conditions, test results that they might have obtained or treatment options for their condition. This may be displayed to a user (at 2560), and may include click activity capture 2570. The Top of Mind knowledge provider 2530 uses the following exemplary criteria to generate a candidate list of search terms that might be considered top of mind for a patient, including:
1. Any items in the chart that might pose a health risk to the patient.
2. Any abnormal or out of range conditions (this could include test results, vital statistics that might be abnormal according to clinical standards, or could be the result of values that indicate potential co-morbidities identified through data mining).
3. Any items that might help in the recovery of patients after clinical procedures like surgery.

4. Any items that are potential treatment options given a patient's current conditions.

FIGS. 26-31 each show screen shots (screens) of the results obtained when executing the various steps hereinabove.

Figure 28:
Figure 30:

For example, FIG. 28 shows a screen shot of a healthcare Provider Guided Patient Education Material. In the care of a patient, the webpage enables a patient to conduct searches across medical conditions and statuses. The search can be restricted by the healthcare provider organization to site specific material that can be available on the web, or can be any media including pamphlets, healthcare guides, prescription information and other multimedia data such as videos and images uploaded specifically for the treatment and care of such patients. These materials can be uploaded by the healthcare providers directly at the point of care through their EHR systems, care managers and other members of a patient's care team can also directly upload education material directly at the point of care and it is made searchable and accessible to the patient.

In addition to specific material uploaded by the healthcare providers or the provider organization, the healthcare providers and provider organization can also guide patient searches to websites that the healthcare provider determines is relevant to the patient's clinical condition.

Some private health plans, such as Medicare Advantage (MA) plans, under a healthcare payer's governing (e.g., Medicare) contract(s), are designed to receive a fixed monthly fee in exchange for providing comprehensive healthcare to plan members. In order to provide appropriate care to beneficiaries with varying medical conditions, plans are paid according to the Risk Adjustment Factor (RAF) score of each patient. RAF scores are computed each reporting year by the governing contract, e.g., Medicare, based on the number of distinct qualified Hierarchical Condition Category (HCC) related, e.g., ICD-9, codes that are documented in a face-to-face encounter and then submitted to the healthcare payer, e.g., Medicare, that year. Insufficient documentation of chronic conditions may become a big obstacle to healthcare plan (e.g., MA) reimbursement. However, even when a condition has been properly documented by the healthcare provider, it is often not coded and submitted to the healthcare payer (e.g., Medicare).

The diagnosis codes submitted on an encounter claim are usually limited to the primary problems addressed during the visit. Additional chronic conditions properly documented by the physician at some point during a reporting year are frequently not included in claim submission. Furthermore, the rules governing whether documentation is sufficient to submit an acceptable code, e.g., an acceptable Medicare Advantage code, are nuanced and not well understood by most clinic-based coders. For example, a condition must be addressed in a face-to-face encounter and the condition status and a care plan must be clearly documented for the patient. The impact of the HCC Coding Problem is that only 60 to 75 percent of sufficiently documented conditions are coded and submitted to the payer (e.g., Medicare) each year, which results in millions of dollars per year in lost reimbursement and an understated view of patient-level risk.

One strategy to minimize the impact of the HCC Coding Problem is to perform manual chart reviews each year. Healthcare organizations that are unable to audit every patient chart may elect to use claims-based strategies to perform a targeted chart review to find documented conditions which are not coded. At a cost of thirty to sixty minutes of coder time per chart, this is an inefficient and expensive approach that results in highly variable results.

In one embodiment of the present invention, the potential impact of text mining are examined to solve the (e.g., Medicare Advantage) HCC Coding Problem. Text mining is the process of analyzing documents with computer algorithms to find specific information. In this embodiment, as illustrated by the example described below, advanced computer-assisted text mining was performed on textual documents, such as encounter notes, and scanned documents, consisting primarily of consult letters, procedure notes and discharge summaries. The text mining algorithm was optimized to find well-formed references to conditions that can impact a patient's RAF score. These conditions identified by text mining are then compared against coded data to expose HCC coding opportunities.

For text mining of clinical information to generate meaningful structured data, it may be necessary for the text mining algorithm to be specifically designed for the application, in this case, finding HCC coding opportunities. Applications for clinical text mining should have the ability to analyze the text in the context of the patient's entire clinical history. Additionally, for a typical healthcare organization with 200,000 patients, it would require 70,000 hours on a single computer to process its textual data, so that a highly scalable, distributed computing analytics architecture becomes critical. Hence, a highly sophisticated, modern computing platform can distribute analytic jobs over a large number of computing nodes to mine coded and unstructured data for a large healthcare system and to return results in minutes.

In one exemplary implementation, a Health Care Association (HCA) provides comprehensive, high-quality care for approximately eight thousand (e.g., Medicare Advantage) healthcare beneficiaries, and proper identification and management of risk can be a key priority. Accordingly, the HCA initiates a text mining study to determine the magnitude of its HCC Coding Problem after determining that the broad diversity of coder training and billing practices among the healthcare provider groups within HCA could lead to a significant loss of revenue due to missed coding opportunities.

Accordingly, data including structured EHR data, text documents, scanned documents and claims data for MA patients is assembled in a cloud-based, highly scalable clinical analytics platform. As part of this process, text from scanned documents can be extracted using Optical Character Recognition (OCR) technology known to one skilled in the art. All text pertaining to encounters that took place in a calendar year is analyzed by a text mining algorithm developed to identify properly documented conditions which represent HCCs. For the (e.g., Medicare Advantage) HCC Coding Problem, the challenge is to mine the documentation from face-to-face encounters with qualified healthcare providers to find descriptions of conditions that satisfy the healthcare payer's (e.g., Medicare's) submission criteria.

HCC relevant conditions found in text were then checked against the, for example, ICD-9 codes already submitted to the payer (e.g., Medicare), taking into account the rules that the healthcare payer uses to combine different HCCs (the "HCC Hierarchy"). Conditions that remained after subtraction of previously claimed codes were presented to coders for review and acceptance. Along with the proposed HCC code, the source document was displayed, with key text highlighted, as illustrated by the screenshot of FIG. 32. The user was given the option to accept or reject the condition, as identified, and, if accepted, to select the proper coding from a targeted list of (e.g., ICD-9) codes.

For the HCC's healthcare plan (e.g., MA) beneficiaries, the HCA originally claimed 4,800 HCC codes. The text mining algorithm identified 760 additional valid HCC codes, an increase of 16%. Accepted opportunities were found to have an average RAF value of 0.32, amounting to an expected $2.3 million of additional reimbursement to the plan. Given that each coder reviewed at least fifty opportunities per hour, his implies an impressive $38,000 reimbursement increase per hour of coder time.

Accordingly, organizations facing the HCC Coding Problem often attempt manual chart review for some or all MA patients. In a separate study, it was determined that a manual chart review of eight thousand plus charts would require about 18 person-months of labor at a cost over $100,000, along with a significant project management effort from the organization.

Hence, computer-assisted text mining can be an effective, accurate and highly cost-effective methodology to solve the healthcare plan (e.g., Medicare Advantage) HCC Coding Problem, allowing healthcare organizations to be more accurately reimbursed for the value-added care that they provide their healthcare plan's beneficiaries, and providing an excellent adjunct to manual chart audits.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. In a Medical Information Navigation Engine ("MINE"), a computerized method for clinical knowledge extraction, the method comprising:
    receiving medical information in various non-standardized encrypted electronic source formats, wherein the medical information includes examiner notes, consult letters, procedure notes and discharge summaries;
    storing the received medical information in a secure cloud-based analysis platform;
    converting the medical information into a standardized computer readable formats by indexing and tagging;
    identifying a plurality of elements with reimbursement potential utilizing a series of servers performing optical character recognition on clinical history by text mining the converted medical information, for conditions that impact a patient's risk adjustment factor (RAF) score using a distributed analysis over a plurality of computing nodes;
    assigning a code to each of the plurality of elements using a coding model;
    subtracting at least one coded element for which reimbursement has already been sought from the plurality of elements, wherein the subtracting is based on at least one business logic;
    sorting a remainder of the plurality elements in accordance with at least one optimization criteria based on clinical history;
    automatically generating a message with the codes assigned to the sorted remainder of the plurality of elements, and source documents associated with these codes from the clinical history, with the remainder of the plurality of elements highlighted within the source documents, to a user for validation;
    transmitting the message in real-time to a user for review;
    validating the codes by manual user review;
    receiving the validation from the user for the codes;
    updating the RAF score for the patient using the number of validated codes for the given patient in a care period; and
    seeking reimbursement for the updated RAF score from a healthcare payer.

2. The computerized method of claim 1 wherein the reimbursement potential includes at least one of contribution to payoff and previously rejected claims.

3. The computerized method of claim 2 wherein the rejected claims were rejected based on at least one of claim duplication, claim invalidity and improper claim format.

4. The computerized method of claim 1 wherein the at least one business logic includes at least one of encounter documentation, code hierarchy supersession and healthcare provider validation.

5. The computerized method of claim 1 wherein the at least one optimization criteria includes at least one of potential for payoff, contribution to patient risk and likelihood of accuracy.

6. The computerized method of claim 5 wherein the potential for payoff is derived from at least one potential reimbursement value.

7. The computerized method of claim 5 wherein the contribution to patient risk includes at least one patient risk adjustment factor (RAF).

8. The computerized method of claim 1 further comprising formatting the processed sorted remainder of the plurality of coded elements into a format acceptable by at least one of a payer and an auditor.

9. The computerized method of claim 1 wherein at least one of the processed sorted remainder of the plurality of coded elements has been validated by the user.

10. The computerized method of claim 1 further comprising tracking at least one of user presentation and user selection.

11. The computerized method of claim 1 further comprising storing the sorted remainder of the plurality of coded elements in a knowledge exchange for future rankings.

12. A Medical Information Navigation Engine ("MINE") configured to extract clinical knowledge for a user, the MINE comprising;
    a Hierarchical Condition Category (HCC) knowledge provider configured to:
    receiving medical information in various non-standardized encrypted electronic source formats, wherein the medical information includes examiner notes, consult letters, procedure notes and discharge summaries;
    storing the received medical information in a secure cloud-based analysis platform;
    converting the medical information into a standardized computer readable formats by indexing and tagging;
    identify a plurality of elements with reimbursement potential utilizing a series of servers performing optical character recognition on clinical history by text mining the converted medical information, for conditions that impact a patient's risk adjustment factor (RAF) score using a distributed analysis over a plurality of computing nodes;
    assigning a code to each of the plurality of elements using a coding model;

subtract at least one coded element for which reimbursement has already been sought from the plurality of elements, wherein the subtracting is based on at least one business logic;

sort a remainder of the plurality elements in accordance with at least one optimization criteria based on clinical history;

a user interface configured to automatically generate a message with the codes assigned to the sorted remainder of the plurality of elements, and source documents associated with these codes from the clinical history, with the remainder of the plurality of elements highlighted within the source documents, to a user for validation, and transmit the message in real-time to a user for review; and a reimbursement system for updating the RAF score for the patient using the number of validated codes for the given patient in a care period, and seeking reimbursement for the updated RAF score from a healthcare payer.

13. The MINE of claim 12 wherein the reimbursement potential includes at least one of contribution to payoff and previously rejected claims.

14. The MINE of claim 13 wherein the rejected claims were rejected based on at least one of claim duplication, claim invalidity and improper claim format.

15. The MINE of claim 12 wherein the at least one business logic includes at least one of encounter documentation, code hierarchy supersession and healthcare provider validation.

16. The MINE of claim 12 wherein the at least one optimization criteria includes at least one of potential for payoff, contribution to patient risk and likelihood of accuracy.

17. The MINE of claim 16 wherein the potential for payoff is derived from at least one potential reimbursement value.

18. The MINE of claim 16 wherein the contribution to patient risk includes at least one patient risk adjustment factor (RAF).

19. The MINE of claim 12 wherein the HCC knowledge provider is further configured to format the processed sorted remainder of the plurality of coded elements into a format acceptable by at least one of a payer and an auditor.

20. The MINE of claim 12 wherein at least one of the processed sorted remainder of the plurality of coded elements has been validated by the user.

21. The MINE of claim 12 wherein the HCC knowledge provider is further configured to track at least one of user presentation and user selection.

22. The MINE of claim 12 further comprising a knowledge exchange configured to store the sorted remainder of the plurality of coded elements for future rankings.

23. In a Medical Information Navigation Engine ("MINE"), a computerized method for hosting provider-guided educational material and top-of-mind concepts for patients, the method comprising;

identifying at least one uncoded item in a patient clinical history;

matching the identified at least one uncoded item with a user hot list;

processing the matched and identified at least one uncoded item in a knowledge exchange, wherein the processing includes:

forming pairs and triples of the at least one uncoded item;

identifying risks between the pairs and triples; and ranking the at least one uncoded item by the risk associated with its pair or triple and click rates;

recording click events for the at least one uncoded item; and updating the click rates based upon the recorded click events.

* * * * *